United States Patent
Watterson et al.

(10) Patent No.: US 7,008,958 B2
(45) Date of Patent: Mar. 7, 2006

(54) 2-SUBSTITUTED 5-OXAZOLYL INDOLE COMPOUNDS USEFUL AS IMPDH INHIBITORS AND PHARMACEUTICAL COMPOSITIONS COMPRISING SAME

(75) Inventors: Scott H. Watterson, Pennington, NJ (US); T. G. Murali Dhar, Newtown, PA (US); Edwin J. Iwanwicz, West Windsor, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 172 days.

(21) Appl. No.: 10/441,849

(22) Filed: May 20, 2003

(65) Prior Publication Data

US 2003/0232866 A1 Dec. 18, 2003

Related U.S. Application Data

(60) Provisional application No. 60/382,128, filed on May 21, 2002.

(51) Int. Cl.
*A61K 31/421* (2006.01)
*C07D 263/30* (2006.01)
*C07D 413/02* (2006.01)

(52) U.S. Cl. .................. 514/374; 548/235; 548/236; 549/49

(58) Field of Classification Search ............. 548/236, 548/235; 514/374; 549/49
See application file for complete search history.

(56) References Cited

U.S. PATENT DOCUMENTS

| | | | |
|---|---|---|---|
| 5,317,103 A | 5/1994 | Baker et al. |
| 5,877,329 A | 3/1999 | Chen et al. |
| 6,353,007 B1 | 3/2002 | Sharma et al. |
| 6,492,385 B1 | 12/2002 | Myers et al. |

FOREIGN PATENT DOCUMENTS

| | | |
|---|---|---|
| EP | 438230 | 4/1997 |
| WO | WO 92/13856 | 8/1992 |
| WO | WO 97/21707 | 6/1997 |
| WO | WO 02/016333 | 2/2002 |

OTHER PUBLICATIONS

Yang et al (1992): STN International CAPLUS database, Columbus, Ohio, Accession No., 1992:633770.*
Quaedflieg et al., "An Alternative Route to the Preparation of (3'→5') Methylene Acetal Linded Di– and Trinucleosides", *Synthesis*, 1993, pp. 627–633.
Yang et al., "Synthesis of some 5–substituted indoles", *Heterocycles*, vol. 34, pp. 1169–1175, 1992.
Zhang et al., "Synthesis of pyrimido[4,5–β]indoles and benzo[4,5]furo[2,3–α]pyrimidines via palladium–catalyzed intramolecular arylation", *Tetrahedron Letters*, vol. 43, pp. 8235–8239, 2002.
Street et al., "Synthesis and Serotonergic Activity of 5–(Oxadiazoly)tryptamines: Potent Agonists for 5–HT$_{1D}$ Receptors", *J. Med. Chem.*, vol. 36, pp. 1529–1538, 1993.
Soares–Santos et al., "Blue–emitting fluorophores bases on 1,3–benzoxazolyl and 1,3–benzothiazolyl–substituted indoles and carbazoles", *Advances in Colour Science and Technology*, vol. 5, pp. 94–98, 2002.

* cited by examiner

*Primary Examiner*—Golam M M Shameem

(57) ABSTRACT

Compounds having the formula (I),

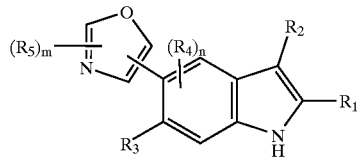

are effective as inhibitors of IMPDH enzyme, wherein $R_3$ is alkyl, substituted alkyl, alkoxy, haloalkoxy, or halogen, preferably methoxy, ethoxy, or trifluoromethoxy; and $R_1$, $R_2$, $R_4$, and $R_5$ are as defined in the specification.

13 Claims, No Drawings

2-SUBSTITUTED 5-OXAZOLYL INDOLE COMPOUNDS USEFUL AS IMPDH INHIBITORS AND PHARMACEUTICAL COMPOSITIONS COMPRISING SAME

CROSS-REFERENCE TO RELATED APPLICATIONS

This application claims the priority benefits of U.S. Provisional Application No. 60/382,128, filed May 21, 2002, all of which is fully incorporated herein by reference.

FIELD OF THE INVENTION

The invention relates to 2-substituted 5-oxazolyl indole compounds that inhibit the activity of IMPDH enzyme. The compounds of the present invention and pharmaceutical compositions containing them advantageously may be used as therapeutic agents for treating disorders associated with the activity of IMPDH.

BACKGROUND OF THE INVENTION

Inosine monophosphate dehydrogenase (IMPDH) has been shown to be a key enzyme in the regulation of cell proliferation and differentiation. IMPDH is involved in the de novo synthesis of guanosine nucleotides, which are required for cells to divide and replicate. Because B and T lymphocytes depend on the de novo pathway, inhibitors of IMPDH have been shown to possess immunosuppressive activities, as well as antineoplastic, antiviral, and antiparasitic activities. IMPDH inhibitors have been proven advantageous in mammals—e.g. the prodrug of MPA (CellCept®) and other IMPDH inhibitors are useful drugs for treating transplant rejection and autoimmune disorders, including HIV. Various other IMPDH inhibitors are in clinical studies, including Vertex compound (VX-497), and/or have been approved for use in humans. See, e.g., Compilation, *Current Medicinal Chemistry*, Vol. 6, No. 7 (July 1999), Contents: Inhibition of Inosine Monophosphate Dehydrogenase (IMPDH), at 519 ("Over 300 literature citations now address the characterization, mechanism, and biological functions of IMPDH, its role as a target for both antileukemic and immunosuppressive therapy, and its inhibition by chemotherapeutic agents.")

As may be appreciated, those in the field of pharmaceutical research continue to seek to develop new compounds and compositions having increased effectiveness and bio-availability and/or having fewer side effects. There is particularly an interest in developing agents that can selectively and directly inhibit key enzymes having significant biological effects such as IMPDH. The present invention provides 2-substituted-5-oxazolyl indole compounds useful as inhibitors of IMPDH. Various aryl or heteroaryl substituted indole compounds useful for other purposes are disclosed in: WO 00/04013, WO 98/55123 and U.S. Pat. No. 5,780,437 to Merck & Co; European Pat. Applic. 581538 to Marck Sharp & Dohme Ltd; Goyal et al., "*Electrochemical Oxidation of 4-Hydroxyindole and Effects of Its Oxidation Products on Blood Parameters of Albino Mice,*" Bioorg. Chem., Vol. 27 (3) (1999), at pp. 239–252; Hiremath et al., "*Synthesis of Substituted 2,5-Bis(Oxadiazolyl/Thiazolidino/Pyrazolyl/Pyrimidinediono)Indoles and Oxadiazolyl/Thiadiazolyl/Triazolyl/Thiazolidinone Analogs of Benzothiophene and their Antibacterial Activity,*" Indian J. Heterocycl. Chem., Vol. 1(4) (1992) at pp. 177–84; and Hiremath et al., "*Synthesis of Substituted 2,5-Bis(1,3,4-Oxadiazolyl/Thiazolidino/1,2,4-Triazolyl)Indoles and Study of their Biological Properties,*" Indian J. Chem., Section B, Vol. 29B(12) (1990) at pp. 1118–24.

SUMMARY OF THE INVENTION

The present invention provides compounds of the following formula (I), their enantiomers, diastereomers, tautomers and pharmaceutically acceptable salts, hydrates, and prodrugs thereof:

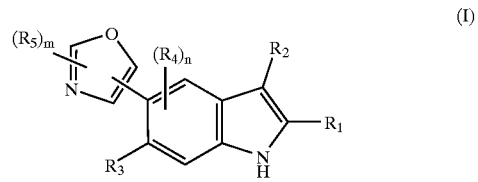

wherein:

$R_1$ and $R_2$ are (i) independently selected from hydrogen, halogen, cyano, alkyl, substituted alkyl, —C(=O)$R_6$, —CO$_2$$R_6$, —S(=O)$R_7$, —SO$_2$$R_7$, —SO$_3$$R_7$, —O$R_6$, —S$R_6$, —N$R_6$$R_7$, —C(=O)N$R_6$$R_7$, —N$R_6$C(=O)$R_7$, N$R_6$CO$_2$$R_7$, —N$R_6$SO$_2$$R_7$, —SO$_2$N$R_6$$R_7$, cycloalkyl, aryl, heterocyclo and heteroaryl, provided that $R_1$ and $R_2$ are not both hydrogen; or (ii) alternatively, $R_1$ and $R_2$ taken together form an optionally-substituted fused ($C_{5-6}$) carbocyclic ring or five-to-six membered heterocyclo ring;

$R_3$ is alkyl, substituted alkyl, alkoxy, haloalkoxy, or halogen;

$R_4$ and $R_5$ are independently selected from alky, substituted alkyl, halogen, cyano, and —O$R_9$;

$R_6$ and $R_7$ are selected from hydrogen, alkyl, substituted alkyl, cycloalkyl, aryl, heterocyclo, and heteroaryl, except $R_7$ is not hydrogen when attached to a sulfonyl group as in —S(=O)$R_7$, —SO$_2$$R_7$, and —SO$_3$$R_7$;

$R_9$ is selected from hydrogen, $C_{1-6}$alkyl, substituted $C_{1-6}$alkyl, cycloalkyl, aryl, heterocyclo, and heteroaryl; and m and n are 0, 1 or 2.

The present invention also provides pharmaceutical compositions comprising the compounds of formula (I) and methods of treating IMPDH-associated disorders using the compounds of formula (I).

DETAILED DESCRIPTION OF EMBODIMENTS OF THE INVENTION

The following are definitions of the terms as used throughout this specification and claims. The initial definition provided for a group or term herein applies to that group or term throughout the present specification, individually or as part of another group, unless otherwise indicated.

The term "alkyl" refers to straight or branched chain hydrocarbon groups having 1 to 12 carbon atoms, preferably 1 to 8 carbon atoms, such as methyl, ethyl, n-propyl, i-propyl, n-butyl, i-butyl, t-butyl, pentyl, hexyl, heptyl, octyl, etc. Lower alkyl groups, that is, alkyl groups of 1 to 4 carbon atoms, are most preferred.

The term "substituted alkyl" refers to alkyl groups substituted with one, two or three groups selected from halogen, cyano, keto (=O), —O$R_a$, —S$R_a$, —N$R_a$$R_b$, —(C=O)$R_a$, —CO$_2$$R_a$, —C(=O)N$R_a$$R_b$, —N$R_a$C(=O)$R_b$, —N$R_a$CO$_2$$R_b$, —OC(=O)$R_a$, —OC(=O)N$R_a$$R_b$, —N$R_c$C(=O)N$R_a$$R_b$, —SO$_2$N$R_a$$R_b$, —N$R_a$SO$_2$$R_d$, —SO$_2$$R_d$, —SO$_3$$R_d$, cycloalkyl, aryl, heteroaryl, and heterocyclo, wherein the groups $R_a$, $R_b$, and $R_c$ are selected from hydrogen, $C_{1-6}$alkyl, cycloalkyl, aryl, heteroaryl, heterocycle, or $C_{1-6}$alkyl or $C_{2-6}$alkenyl substituted with one, two or three of halogen, hydroxy, O(alkyl), haloalkoxy, O(phenyl), O(benzyl), nitro, cyano, —(C=O)H, —CO$_2$H, —(C=O)alkyl, —CO₂alkyl, —(C=O)cycloalkyl, —CO₂cycloalkyl, —C(=O)phenyl, —CO₂phenyl, —NH₂, —NH(alkyl), —N(alkyl)₂, —NH(cycloalkyl), —NH(aryl), —NH(heterocyclo), —SH, —S(alkyl), —(C=O)NH₂, —(C=O)NH(alkyl), —(C=O)NH(cycloalkyl), —(C=O) N(alkyl)₂, SO₂(alkyl), phenyl, benzyl, C₃₋₇cycloalkyl, four to seven membered heterocyclo, and/or five or six membered heteroaryl. The group R_d may be selected from the same groups as. R_a, R_b and R_c, but is not hydrogen. Alternatively, the groups R_a and R_b may together form a heterocyclo or heteroaryl ring. It should be understood that when a substituted alkyl group is substituted with an aryl, cycloalkyl, heteroaryl, or heterocyclo, such rings are as defined below and thus may have one to three substituents as set forth below in the definitions for these terms.

When the term "alkyl" is used as a suffix following another specifically-named group, e.g., arylalkyl, heteroarylalkyl, hydroxyalkyl, the term defines with more specificity at least one of the substituents that the substituted alkyl will contain. For example, arylalkyl refers to an aryl bonded through an alkyl, or in other words, a substituted alkyl group having from 1 to 12 carbon atoms and at least one substituent that is aryl (e.g., benzyl or biphenyl). "Lower arylalkyl" refers to substituted alkyl groups having 1 to 4 carbon atoms and at least one aryl substituent. It should be understood that when reference is made to an arylalkyl, heteroarylalkyl, cycloalkylalkyl, or heterocycloalkyl, the ringed groups are as defined below and thus may optionally be substituted, as defined below.

When a subscript is used in conjunction with a group such as C₁₋₄alkyl, the subscript refers to the number of carbon atoms that the group will contain, in addition to heteroatoms. Thus, the term hydroxyC₁₋₄alkyl or C₁₋₄hydroxyalkyl refers to an alkyl group of one to four carbon atoms having an OH substituent on one of the carbon atoms. As another example, the term C₁₋₂alkylamino refers to an alkylamino group having one or two carbon atoms, i.e., NHCH₃, N(CH₃)₂, or NHCH₂CH₃.

The term "alkenyl" refers to straight or branched chain hydrocarbon groups having 2 to 12 carbon atoms and at least one double bond. Alkenyl groups of 2 to 6 carbon atoms and having one double bond are most preferred.

The term "alkynyl" refers to straight or branched chain hydrocarbon groups having 2 to 12 carbon atoms and at least one triple bond. Alkynyl groups of 2 to 6 carbon atoms and having one triple bond are most preferred. A "substituted alkenyl" or "substituted alkynyl" will contain one, two, or three substituents as defined above for alkyl groups.

The term "alkylene" refers to bivalent straight or branched chain hydrocarbon groups having 1 to 12 carbon atoms, preferably 1 to 8 carbon atoms, e.g., {—CH₂—}_n, wherein n is 1 to 12, preferably 1–8. Lower alkylene groups, that is, alkylene groups of 1 to 4 carbon atoms, are most preferred. The terms "alkenylene" and "alkynylene" refer to bivalent radicals of alkenyl and alknyl groups, respectively, as defined above. Substituted alkylene, alkenylene, and alkynylene groups may have substituents as defined above for the monovalent groups.

The term "alkoxy" refers to the group OR_e wherein R_e is alkyl, substituted alkyl, alkenyl, substituted alkenyl, heterocycle, or cycloalkyl. Thus, an alkoxy includes such groups as methoxy, ethoxy, cyclopropyloxy, pyrrolidinyloxy, and so forth. The term "aryloxy" refers to the groups O(aryl) and O(heteroaryl), wherein aryl and heteroaryl are as defined below. A substituted alkoxy or aryloxy will have one, two or three substituents as defined herein for the respective alkyl, aryl or heteroaryl group.

The term "alkylthio" refers to an alkyl or substituted alkyl group as defined above bonded through one or more sulfur (—S—) atoms, e.g., —S(alkyl) or —S(substituted alkyl).

The term "alkylamino" refers to the groups —NHR_f and NR_fR_g, wherein R_f and R_g are alkyl or substituted alkyl as defined above. "Aminoalkyl" refers to an amino group bonded through an alkyl, e.g., —(CH₂)_x—NH₂. "Alkylaminoalkyl" refers to an alkylamino group (i.e., —NHR_f or NR_fR_g) bonded through an alkyl group (e.g., —(CH₂)_x— NHR_f or —(CH₂)_x—NR_fR_g).

The term "acyl" refers to an alkyl or substituted alkyl group as defined above bonded through one or more carbonyl {—C(=O)—} groups. When the term acyl is used in conjunction with another group, as in acylamino, this refers to the carbonyl group {—C(=O)} linked to the second named group. Thus, for example, acylamino refers to —C(=O)NH₂ and acylaryl refers to —C(=O)(aryl).

The term "halo" or "halogen" refers to chloro, bromo, fluoro and iodo.

The term carbamyl refers to the group C(=O)NR_hR_i wherein R_h and R_i may be selected from hydrogen, alkyl, and substituted alkyl.

The term "carboxy" when used alone refers to the group CO₂H. "Carboxyalkyl" refers to the group CO₂R_f, wherein R_f is alkyl or substituted alkyl, as defined above.

The term "sulfonamide" or "sulfonamidyl" refers to the group —S(O)₂NR_hR_i, wherein R_h and R_i are as defined above for carbamyl.

The term "sulphonyl" or "sulfonyl" refers to the group —S(O)₁₋₂R_f, wherein R_f is alkyl or substituted alkyl, as defined above.

The term "cycloalkyl" refers to monocyclic or bicyclic hydrocarbon groups of 3 to 9 carbon atoms which are, respectively, fully saturated or partially unsaturated. The term "cycloalkyl" includes such saturated or partially unsaturated carbocyclic rings having a carbon-carbon bridge of three to four carbon atoms or having 1 or 2 aromatic or heterocyclo rings fused thereto. Thus, the term "cycloalkyl" thus includes, for example, cyclopropyl, cyclobutyl, cyclopentyl, cyclohexyl, cycloheptyl, cyclooctyl, etc., as well as

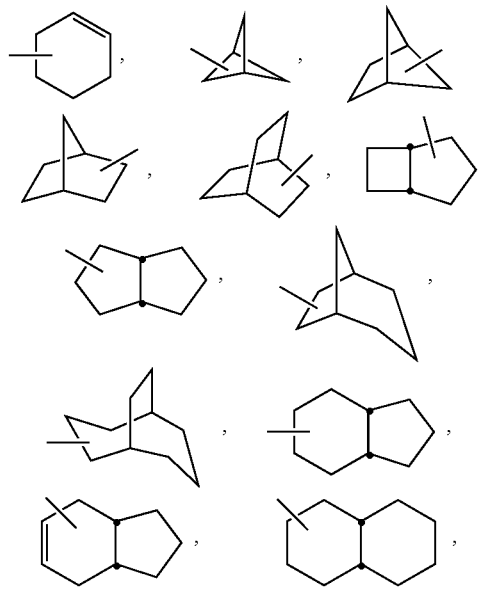

-continued

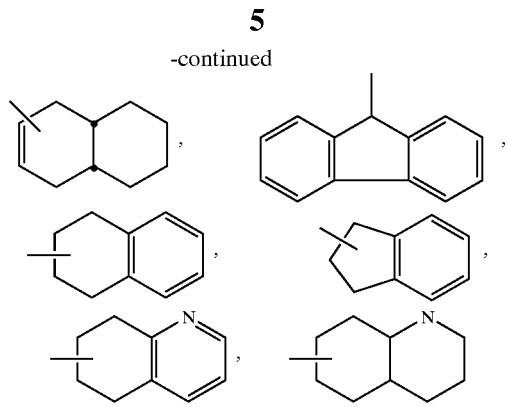

and the like.

Additionally, the term "cycloalkyl" unless otherwise indicated includes cycloalkyl groups as defined above substituted with one, two or three groups selected from (i) $R_j$, (ii) keto (=O), and (iii) $C_{1-6}$alkyl or $C_{2-6}$alkenyl optionally substituted with one to three of $R_j$, wherein $R_j$ is halogen, nitro, cyano, haloalkyl, haloalkoxy, —O-A-$R_k$, —S-A-$R_k$, —C(=O)-A-$R_j$, —OC(=O)-A-$R_k$, —S(=O)-A-$R_k$, —SO$_2$-A-$R_k$, —CO$_2$-A-$R_k$, —NR$_j$-A-$R_k$, —NR$_m$C(=O)-A-$R_k$, —NR$_m$C(=O)NR$_n$-A-R—$R_k$, —NR$_m$CO$_2$-A-$R_k$, —NR$_m$SO$_2$-A-$R_k$, —NR$_m$SO$_2$NR$_n$-A-$R_k$, —SO$_2$NR$_m$-A-$R_k$, or —C(=O)NR$_m$-A-$R_k$, phenyl or benzyl substituted with one to two $R_p$, $C_{3-7}$ cycloalkyl substituted with keto(=O) and/or one to two $R_p$, four to seven membered monocyclic or seven to eleven membered bicyclic heterocyclo substituted with keto(=O) and/or one to two $R_p$, and five to six membered monocyclic or nine or ten membered bicyclic heteroaryl substituted with one to two $R_p$, wherein A is —(CR$_m$R$_n$)$_w$—; w is 0 to 4; $R_m$ and $R_n$ are selected from hydrogen, alkyl, hydroxyalkyl, haloalkyl, amino, and aminoalkyl; $R_k$ is selected from hydrogen, alkyl, amino, alkylamino, phenyl, $C_{3-7}$ cycloalkyl, four to seven membered monocyclic or seven to eleven membered bicyclic heterocyclo, and five to six membered monocyclic or nine or ten membered bicyclic heteroaryl; wherein each $R_k$ in turn is optionally substituted with one to two $R_p$, and $R_p$ is at each occurrence independently selected from $C_{1-4}$alkyl, $C_{2-4}$alkenyl, —O($C_{1-4}$alkyl), —O($C_{1-4}$alkyl), halogen, cyano, nitro, —$C_{1-4}$haloalkyl, —O($C_{1-4}$haloalkyl), —SH, —S($C_{1-4}$alkyl), —SO$_2$($C_{1-4}$alkyl), —CO$_2$H, —CO$_2$($C_{1-4}$ alkyl), —C(=O)H, —C(=O)($C_{1-4}$alkyl), —NH$_2$, —NH ($C_{1-6}$alkyl), —N($C_{1-6}$alkyl)$_2$, phenyloxy, benzyloxy, and/or lower alkyl substituted with one to two hydroxy, halogen, cyano, —O($C_{1-4}$alkyl), —O($C_{2-4}$alkenyl), amino, $C_{1-4}$alkylamino, nitro, trifluoromethyl, trifluoromethoxy, —S($C_{1-4}$alkyl), —SO$_2$$C_{1-4}$alkyl, —CO$_2$H, —CO$_2$($C_{1-4}$ alkyl), —C(=O)H, and/or —C(=O)($C_{1-4}$alkyl).

The term "aryl" refers to phenyl, 1-naphthyl and 2-naphthyl, with phenyl being preferred, as well as such rings having fused thereto a cycloalkyl, cycloalkenyl, heterocyclo, or heteroaryl ring. Examples of aryl groups include, without limitation:

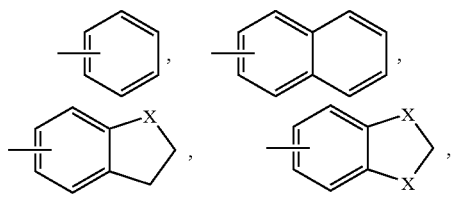

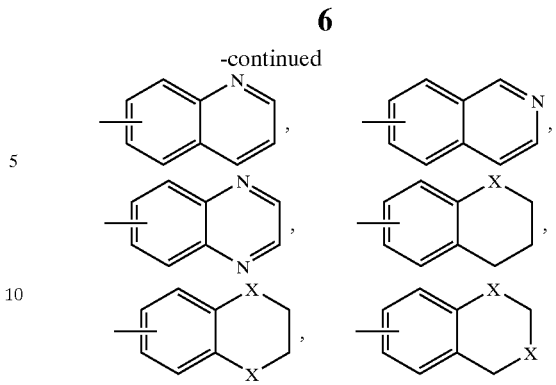

wherein X at each occurrence is selected from oxygen, nitrogen, and sulfur; and other like ring systems.

Additionally, the term "aryl" includes such rings having one, two or three substituents selected from (i) $R_j$, and (ii) $C_{1-6}$alkyl or $C_{2-6}$alkenyl optionally substituted with one to two of $R_j$ and/or keto (=O), wherein $R_j$ is as defined above for cycloalkyl and has the various optional substituents as defined above for cycloalkyl. When reference is made generally to a particular aryl, such as phenyl, it should be understood that unless otherwise indicated, such group may likewise have one, two or three substituents as defined for aryl.

The term "carbocyclo" or "carbocyclic" refers to a cyclic group in which all ring atoms are carbon, including substituted or unsubstituted cycloalkyl and aryl groups, as defined herein.

The term "heterocyclo" or "heterocycle" refers to nonaromatic 3 to 7 membered monocyclic groups, 7 to 11 membered bicyclic groups, and 10 to 15 membered tricyclic groups which have at least one heteroatom (O, S or N) in at least one of the rings. Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. Advantageously, adjacent heteroatoms will not be simultaneously selected from N and O. The rings completing the bicyclic and tricyclic groups may contain only carbon atoms and may be saturated, partially saturated, or unsaturated, and they may be either fused, bridged, and/or joined through one or more spiro unions. The nitrogen and sulfur atoms may optionally be oxidized and the nitrogen atoms may optionally be quaternized. The heterocyclo group may be attached at any available nitrogen or carbon atom. Exemplary heterocyclo groups include, without limitation:

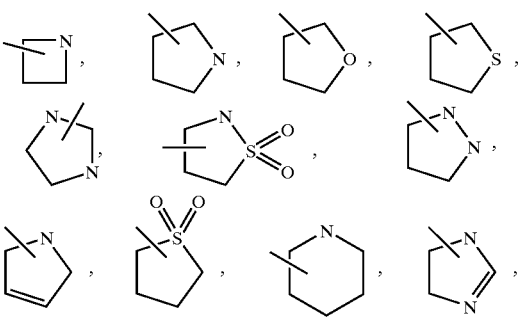

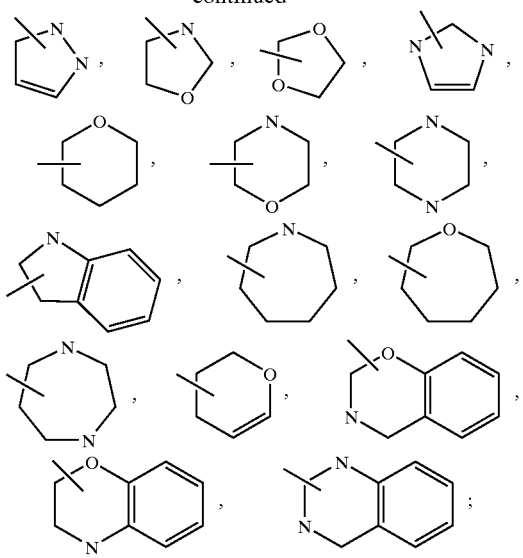

and the like.

The term "heterocyclo" includes heterocyclo rings as defined containing one, two or three substituents at any available carbon or nitrogen atom selected from $R_j$, keto (=O), and $C_{1-6}$alkyl or $C_{2-6}$alkenyl optionally substituted with one to two of $R_j$ and/or keto (=O), wherein $R_j$ is as defined above for cycloalkyl and has the various optional substituents as defined above for cycloalkyl.

The term "heteroaryl" refers to aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms, provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quatemized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. Examples of heteroaryl rings include, without limitation:

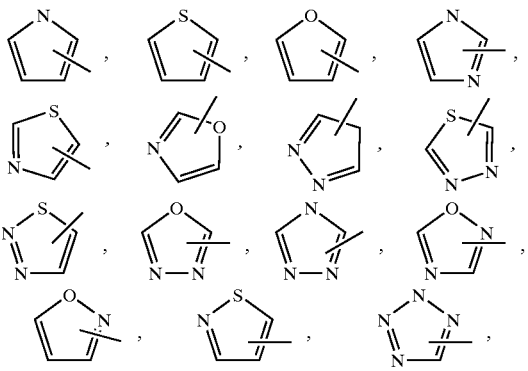

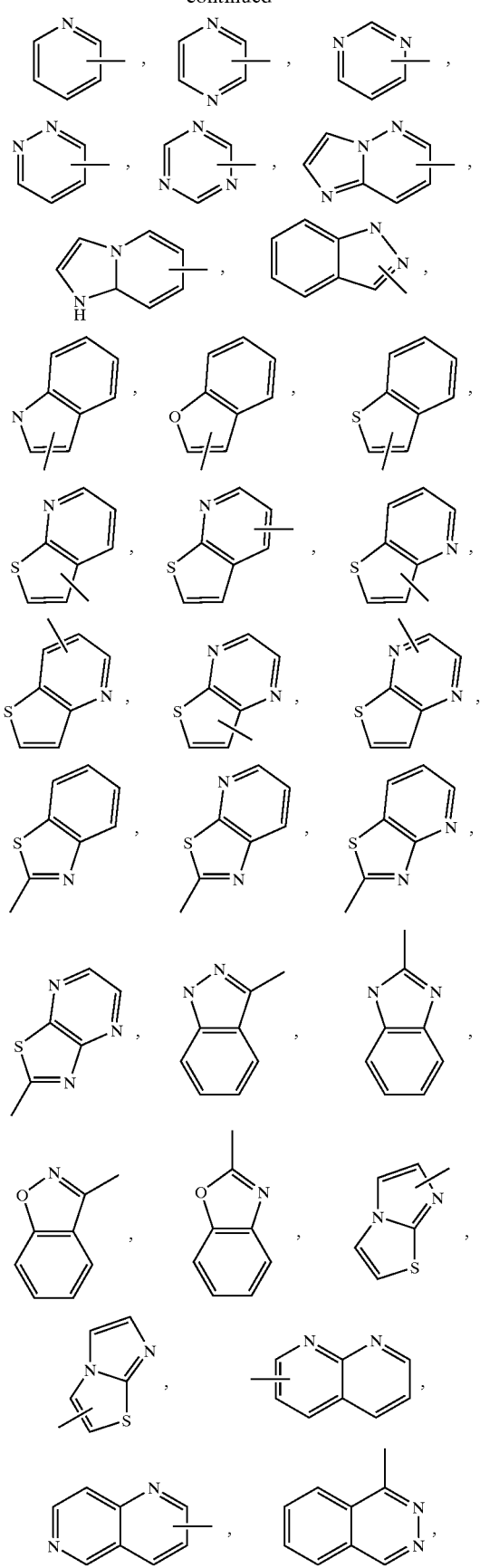

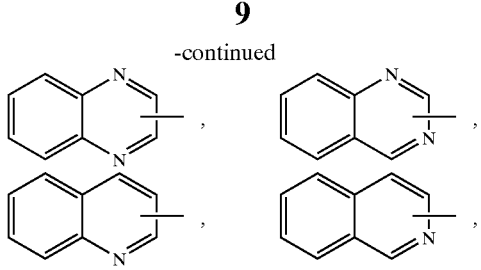

and the like.

The term "heteroaryl" further includes such rings as defined above containing one, two or three substituents at any available carbon or nitrogen atom selected from (i) $R_j$, and (ii) $C_{1-6}$alkyl or $C_{2-6}$alkenyl optionally substituted with one to two of $R_j$ and/or keto (=O), wherein $R_i$ is as defined above for cycloalkyl and has the various optional substituents as defined above for cycloalkyl. When reference is made generally to a particular heteroaryl, such as thienyl or benzothienyl, it should be understood that unless otherwise indicated, such group may likewise have one, two or three substituents as defined for heteroaryl.

The term "heteroatoms" shall include oxygen, sulfur and nitrogen.

The term "haloalkyl" means an alkyl having one or more halo substituents. Thus, it includes, for example, trifluoromethyl.

The term "haloalkoxy" means an alkoxy group having one or more halo substituents. For example, "haloalkoxy" includes —$OCF_3$.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds.

The compounds of Formula (I) may form salts with alkali metals such as sodium, potassium and lithium, with alkaline earth metals such as calcium and magnesium, with organic bases such as dicyclohexylamine, tributylamine, pyridine and amino acids such as arginine, lysine and the like. The compounds for Formula (I) may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art. Salt forms of the compounds may be advantageous for improving the compound dissolution rate and oral bioavailability. Pharmaceutically-acceptable salts are preferred although other salts may be useful, e.g., as intermediates to prepared pharmaceutically-acceptable salts.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of the Formula (I) may also have prodrug forms. Any compound that will be converted in vivo to provide the bioactive agent (i.e., a compound of formula I) is a prodrug within the scope and spirit of the invention.

Various forms of prodrugs are well known in the art. For examples of such prodrug derivatives, see:

a) *Design of Prodrugs*, edited by H. Bundgaard, (Elsevier, 1985) and *Methods in Enzymology*, Vol.42, p. 309–396, edited by K. Widder, et al. (Acamedic Press, 1985);

b) *A Textbook of Drug Design and Development*, edited by Krosgaard-Larsen and H. Bundgaard, Chapter 5, "Design and Application of Prodrugs," by H. Bundgaard, pp. 113–191 (1991); and c) H. Bundgaard, *Advanced Drug Delivery Reviews*, 8, 1–38 (1992), each of which is incorporated herein by reference.

It should further be understood that solvates (e.g., hydrates) of the compounds of Formula (I) are also with the scope of the present invention. Methods of solvation are generally known in the art.

EMBODIMENTS OF THE INVENTION

Compounds according to the invention are those having the formula (Ib):

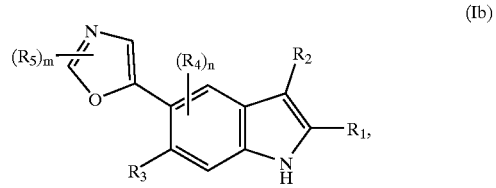

and pharmaceutically-acceptable salts, hydrates, and prodrugs thereof, wherein:

$R_1$ and $R_2$ are (i) independently selected from hydrogen, halogen, cyano, alkyl, substituted alkyl, —C(=O)$R_6$, —CO$_2R_6$, —S(=O)$R_7$, —SO$_2R_7$, —SO$_3R_7$, cycloalkyl, aryl, heterocyclo and heteroaryl, provided that $R_1$ and $R_2$ are not both hydrogen; or (ii) alternatively, $R_1$ and $R_2$ taken together form an optionally-substituted fused ($C_{5-6}$) carbocyclic ring or five-to-six membered heterocyclo ring;

$R_3$ is lower alkyl, lower alkoxy, halo$C_{1-4}$alkoxy, or halogen;

R4 and $R_5$ are independently selected from lower alkyl, substituted lower alkyl, halogen, cyano, and —O($C_{1-4}$ alkyl);

$R_6$ and $R_7$ are selected from hydrogen, alkyl, substituted alkyl, cycloalkyl, aryl, heterocyclo, and heteroaryl, except $R_7$ is not hydrogen when attached to a sulfonyl group as in —S(=O)$R_7$, —SO$_2R_7$, and —SO$_3R_7$; and m and n are 0, 1 or 2.

In another embodiment, compounds of formula (I), including formulae (Ia) set forth hereinafter and (Ib) set forth immediately above, $R_4$ and $R_5$ are absent (m and n are 0), or one or both are selected from lower alkyl.

In another embodiment, compounds of formula (I), including formulae (Ia) and (Ib) herein, $R_1$ is selected from optionally-substituted aryl, heteroaryl, arylalkyl, and heteroarylalkyl. In another embodiment, $R_1$ is selected from phenyl, thienyl, thiazolyl, benzothienyl, and benzyl, and is optionally substituted with one to two groups selected from alkyl, alkenyl, halogen, haloalkyl, haloalkoxy, cyano, nitro, phenyl, benzyl, amino, alkylamino, aminoalkyl, hydroxy, hydroxyalkyl, alkoxy, alkylthio, phenyloxy, and benzyloxy. Another embodiment has compounds where $R_1$ is

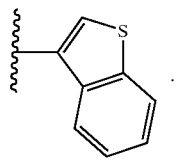

In another embodiment, compounds of formula (I), including formulae (Ia) and (Ib) herein, $R_2$ is selected from hydrogen, halogen, cyano, alkyl, substituted alkyl, —C(=O)$R_6$, —CO$_2$R$_6$, —S(=O)$R_7$, —SO$_2$R$_7$, and —SO$_3$R$_7$, wherein $R_6$ and $R_7$ are as defined above, more preferably hydrogen (for $R_6$) and lower alkyl. Advantageously, $R_2$ will not be selected from an alkyl substituted with NR$_{18}$R$_{19}$, wherein $R_{18}$ and $R_{19}$ are selected from hydrogen, alkyl, or substituted alkyl, or where $R_{18}$ and $R_{19}$ are selected from hydrogen, arylalkyl, heteroarylalkyl, carboxyalkyl, and C(=O)arylalkyl.

In another embodiment, compounds of formula (I), including formulae (Ia) and (Ib) herein, $R_3$ is O(C$_{1-4}$alkyl) or OCF$_3$, alternatively, methoxy or ethoxy.

Also, in another embodiment, are compounds having the formula (Ia), or pharmaceutically-acceptable salts, hydrates, or prodrugs thereof,

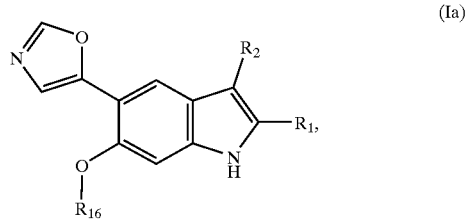

(Ia)

wherein
$R_1$ is selected from phenyl, thienyl, thiazolyl, benzothienyl, and benzyl, optionally-substituted with one to two $R_{15}$, and
$R_2$ is independently selected from hydrogen, halogen, cyano, —C(=O)H, —CO$_2$H, —C(=O)(C$_{1-4}$alkyl) and —CO$_2$(C$_{1-4}$alkyl),
or alternatively, $R_1$ and $R_2$ taken together form a fused, partially saturated (C$_{5-6}$)carbocyclic ring optionally substituted with keto (=O) or a group $R_8$;
$R_8$ and $R_{15}$ are at each occurrence independently selected from alkyl, alkenyl, halogen, haloalkyl, haloalkoxy, cyano, nitro, phenyl, benzyl, amino, alkylamino, aminoalkyl, hydroxy, hydroxyalkyl, alkoxy, alkylthio, phenyloxy, and benzyloxy;
$R_{16}$ is selected from C$_1$–C$_4$alkyl and haloC$_1$–C$_4$alkyl; and p is 0, 1 or 2.

In another embodiment, when $R_1$ and $R_2$ taken together form a fused, partially saturated (C$_{5-6}$)carbocyclic ring, said ring is selected from:

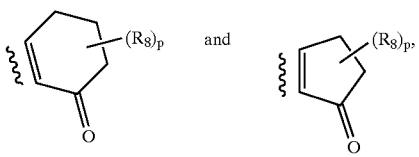

which is fused to ring A sharing a common double bond therewith along the bond region designated with the symbol In another embodiment, are compounds according to formula (Ia), as immediately defined above, wherein $R_{16}$ is methyl or ethyl; $R_1$ is

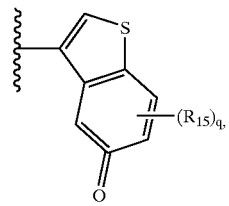

and q is 0, 1 or 2. Also, in another embodiment are compounds where $R_2$ is cyano.

Method of Preparation

The compounds of the present invention may be synthesized using conventional techniques known in the art. Advantageously, these compounds are conveniently synthesized from readily available starting materials. Following are general synthetic schemes for manufacturing compounds of the present invention. These schemes are illustrative and are not meant to limit the possible techniques one skilled in the art may use to manufacture compounds disclosed herein. Different methods will be evident to those skilled in the art. Additionally, the various steps in the synthesis may be performed in an alternate sequence to give the desired compound(s). The groups $R_1$, $R_2$, $R_3$, $R_4$, etc., in the synthetic schemes below are intended to designate the groups as recited in the claims. All documents cited herein are incorporated herein by reference in their entirety.

Compounds of the present invention can be made by many methods known to one skilled in the art of organic chemistry. In general, the time taken to complete a reaction procedure will be judged by the person performing the procedure, preferably with the aid of information obtained by monitoring the reaction by methods such as HPLC or TLC. A reaction does not have to go to completion to be useful to this invention. The preparation of heterocycles useful to this invention is described in the literature, e.g., Katritzky and Rees (Eds.), *Comprehensive Heterocyclic Chemistry. The Structure, Reactions, Synthesis and Uses, of Heterocyclic Compounds*, (Pergamon Press New York, First edition, 1984) (hereinafter "Comprehensive Heterocyclic Chemistry"); and Katritzky, Rees and Scriven (Eds.), *Comprehensive Heterocyclic Chemistry II. A Review of the Literature 1982–1995. The Structure, Reactions, Synthesis and Uses, of Heterocyclic Compounds*, (Pergamon Press New York, 1996).

Amines such as anilines or heterocyclic amines useful to prepare compounds of this invention may be commercially available or readily prepared by methods known to one skilled in the art of organic chemistry. See Larock, *Comprehensive Organic Transformations. A Guide to Functional Group Preparation*, (VCH Publishers, Inc. 1989), at pp. 385–439. Examples include, but are not limited to, reduction of a nitro group and reduction of an azide.

Scheme 1a

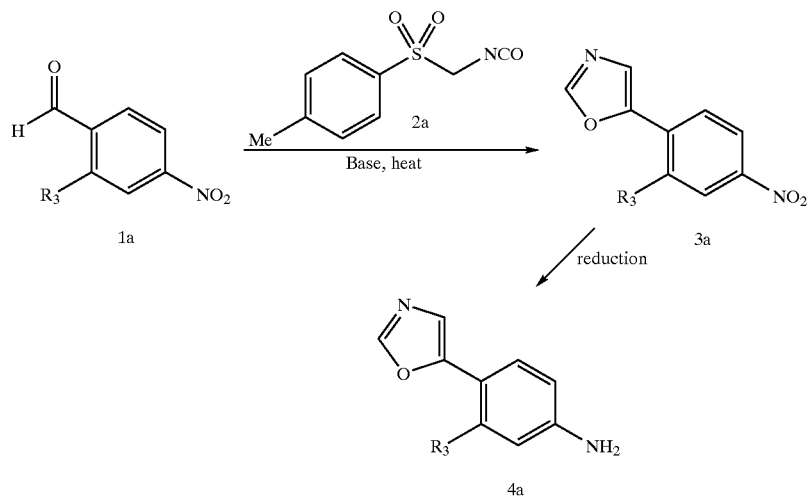

Scheme 1a shows methods for making (5-oxazole) functionalized anilines (4a) useful as intermediates to make compounds of the invention.

1,3-Dipolar cycloaddition of benzaldehydes (1a) and (p-tolylsulfonyl)methyl isocyanate (TOSMIC) (2a) in the presence of a base produces 4-nitrophenyl oxazoles (3a). A variety of bases can be used for the condensation including, but not limited to, potassium carbonate and 1,8-diazabicyclo[5.4.0]undec-7-ene. Benzaldehydes (1a) may be commercially available or prepared from the corresponding methylbenzene by oxidation with reagents such as $CrO_3$, $MnO_2$, and ammonium cerium (IV) nitrate by methods well known to one skilled in the field and described in Hudlicky, *Oxidations in Organic Chemistry*, (ACS Monograph 186, American Chemical Society, Washington, D.C., 1990). The 1,3-dipolar cycloaddition reaction is well known to one skilled in the art and described in Padwa (Ed.), 1,3-*Dipolar Cycloaddition Chemistry*, Vols. 1 and 2, (John Wiley and Sons, New York, N.Y., 1984).

The nitro group in compounds (3a) can be reduced to an amine to provide anilines (4a), as discussed above.

Scheme 1b

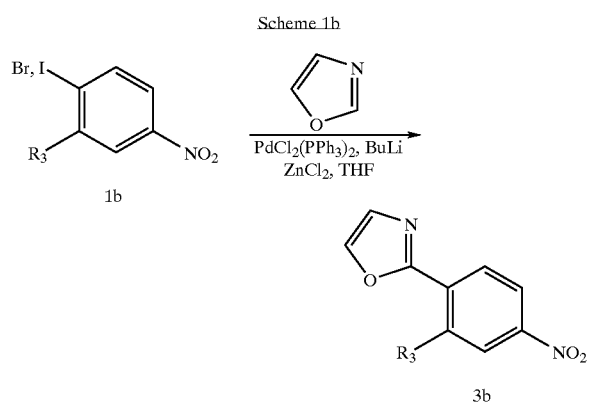

Nitrobenzene compounds (1b) can undergo a palladium-catalyzed cross-coupling reaction with oxazol-2-ylzinc chloride derivatives to produce (2-oxazole) nitrobenzene compounds (3b) (see, e.g., Anderson, et al. *Synthesis*, (1996), at p. 583). Reduction of the nitro group of (3b) as shown in Scheme (1a) produces the corresponding (2-oxazole) anilines.

Scheme 1c

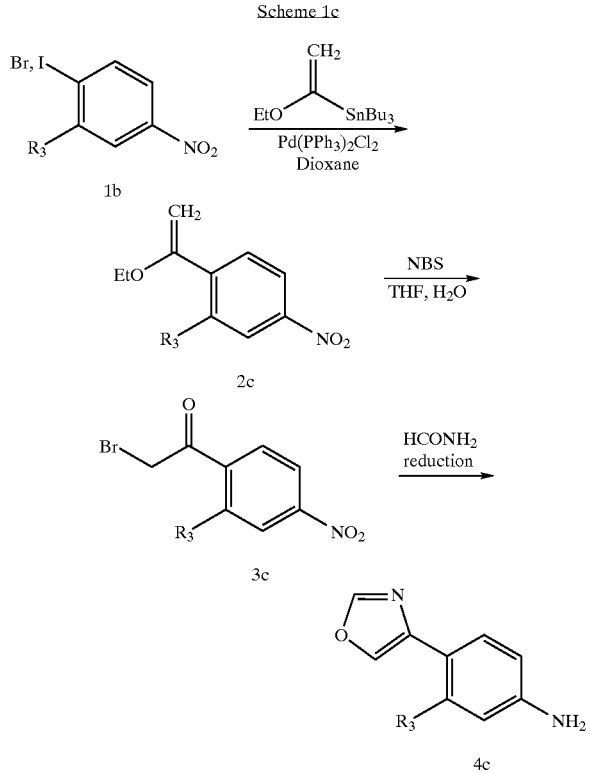

Scheme (1c) shows a general method to prepare (4-oxazole) functionlized anilines (4c). Palladium-catalyzed coupling of a vinyl tin reagent with nitrobenznes (1b) gives vinyl ether (2c). Bromination produces compounds (3c). Subsequent condensation of (3c) with formamide yields the desired (4-oxazole) functionalized nitrobenzene compounds, and then reduction of the nitro group provides anilines (4c). See also Whitney et al., *J. Org. Chem.*, Vol. 55 (1990), at p. 929, for an alternative approach.

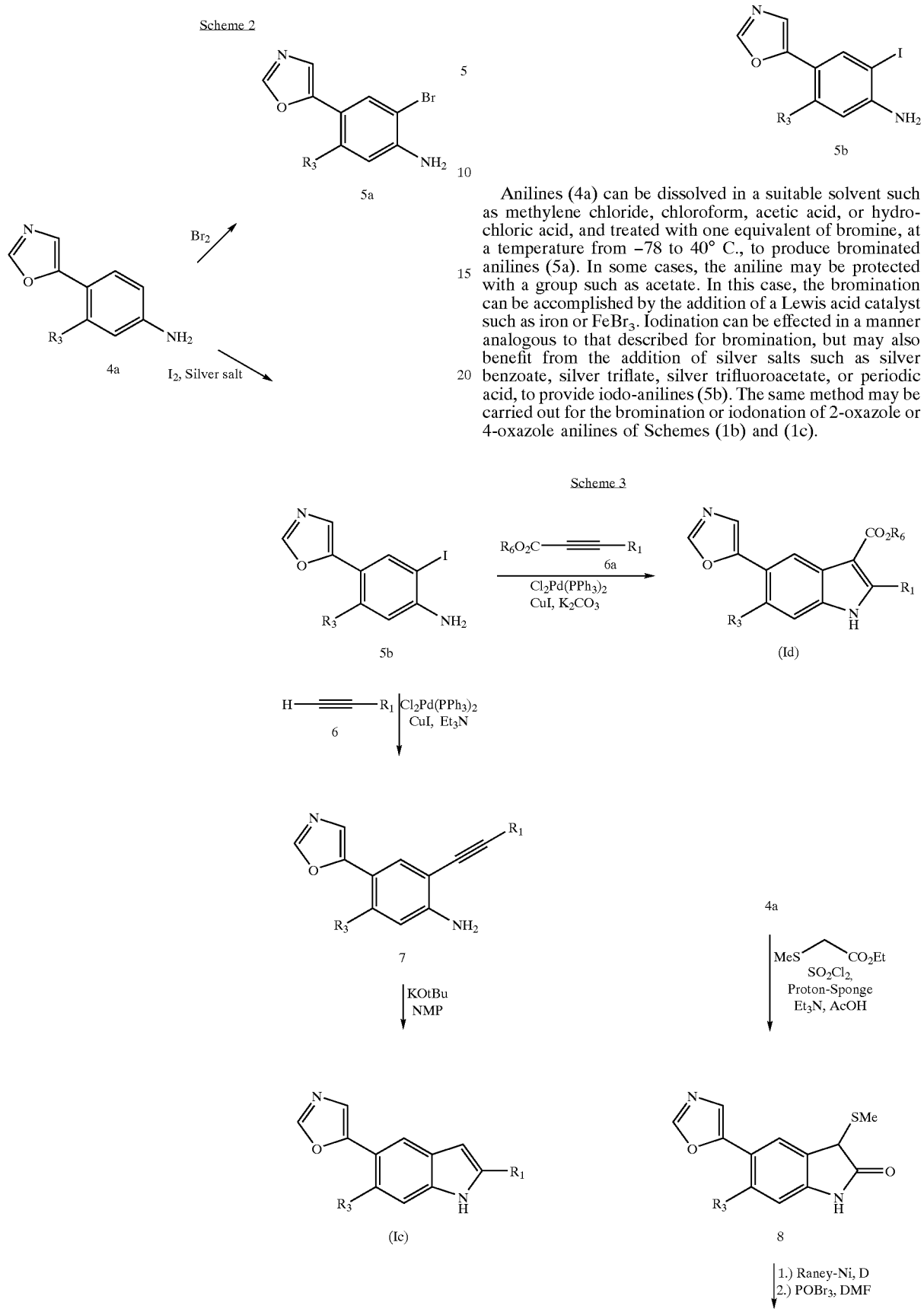

Anilines (4a) can be dissolved in a suitable solvent such as methylene chloride, chloroform, acetic acid, or hydrochloric acid, and treated with one equivalent of bromine, at a temperature from −78 to 40° C., to produce brominated anilines (5a). In some cases, the aniline may be protected with a group such as acetate. In this case, the bromination can be accomplished by the addition of a Lewis acid catalyst such as iron or $FeBr_3$. Iodination can be effected in a manner analogous to that described for bromination, but may also benefit from the addition of silver salts such as silver benzoate, silver triflate, silver trifluoroacetate, or periodic acid, to provide iodo-anilines (5b). The same method may be carried out for the bromination or iodonation of 2-oxazole or 4-oxazole anilines of Schemes (1b) and (1c).

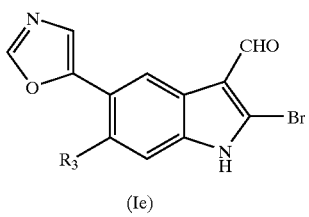

(Ie)

Scheme 3 shows alternative methods for making compounds of formula (I), starting with compound (5b).

Aniline (5b) is heated with an appropriately-substituted acetylene (6) in a basic solvent such as TEA with or without a co-solvent such as dioxane or THF up to the boiling point of the solvent in the presence of a palladium catalyst such as dichlorobis(diphenylphospine)palladium (II) and copper iodide to provide the acetylene (7). Subsequent heating of (7) in N-methylpyrollidine in the presence of a base like potassium t-butoxide affords compounds of formula (Ic). See, e.g., Knochel et al., Angew. Chem. Int. Ed., Vol. 39 (2000), at p. 2488.

A similar procedure may be carried out to provide esters of formula (Id) (wherein $R_6 \neq$ hydrogen), by treating aniline (5b) with an appropriately-substituted pripiolate derivative (6a) in a solvent such as DMF in the presence of dichlorobis(triphenylphospine)palladium (II) and a base such as potassium carbonate. The ester may be hydrolyzed to provide compounds of formula (Id), wherein $R_6$=hydrogen, by methods known in the art including lithium hydroxide and sodium hydroxide hydrolysis (see March (Ed), Advanced Organic Chemistry, (John Wiley and Sons, Inc., New York, N.Y., 1992).

Alternatively, compounds of formula (Ie) wherein the group $R_1$ is bromine may be prepared proceeding through a modified Gassman oxindole synthesis to give intermediate (8) (see e.g., McWhorter et al., J. Org. Chem., Vol. 61 (1996), at page 8696). Further conversion to indole (Ie) was accomplished using a Vilsmeier-Haack formalation reaction.ds Acetylenes (6), (6a), are either commercially available or may be prepared by several methods including palladium-catalyzed coupling with an aryl or vinyl bromide or iodide with trimethylsilylacetylene as described in Takahashi et. al., Synthesis (1980), at p. 627. The trimethylsilyl protecting group can be removed by treatment with aqueous base or with a fluoride source such as tetrabutylammonium fluoride. Alternatively, terminal acetylenes may be synthesized using the Corey-Fuchs synthesis (see, e.g., Wang et al., J. Org. Chem., Vol. 65 (2000), at pp 1889–91 and references contained within). The Corey-Fuchs synthesis and its modifications start with an appropriately-substituted aldehyde. Aldehydes useful for this invention are either commercially available or can be readily prepared by oxidation of an alcohol as described, for example, in Hudlicky, "Oxidations in Organic Chemistry," cited above.

Further alternative methods for the preparation of indoles useful for this invention are detailed in Gribble, "Recent Developments in Indole Ring Synthesis—Methodology and Application," J. Chem. Soc., Perkin Trans., Vol 1, (2000), at 1045; Li et al. (Baldwin et als., Eds.), Tetrahedron Organic Chemistry Series: Palladium in Heterocyclic Chemistry, Vol. 20 (Elsevier Science, Oxford [2000]) at p. 73; and Comprehensive Heterocyclic Chemistry, cited above.

Scheme 4a

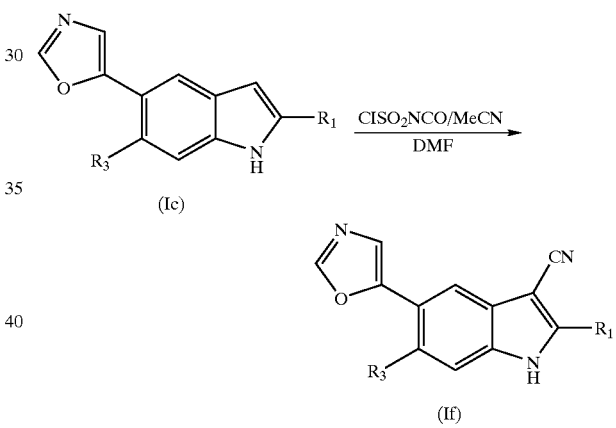

Schemes 4a through 4c show alternative methods for making indoles of formula (I) having various substitutions at the three-position. In Scheme 4a, indoles of formula (Ic) are substituted with a nitrile by treatment with chlorosulfonyl isocyanate in a solvent such as DMF or acetonitrile followed by subsequent heating in the presence of sodium hydroxide, to give cyano-indoles of formula (If).

Scheme 4b

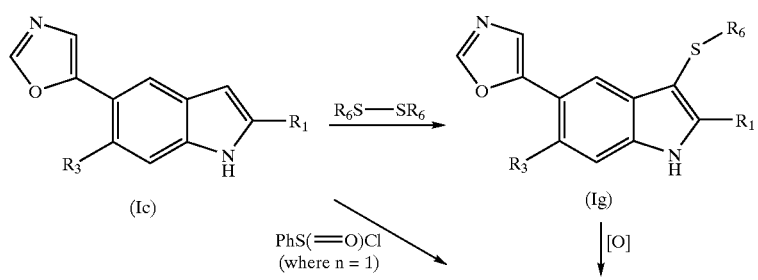

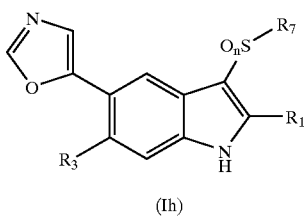

(Ih)

In Scheme 4b, indoles (Ic) are substituted with sulfur by treatment with an alkyl disulfide under various conditions (see, e.g., Atkinson et al., *Synthesis*, Vol. 6 [1988], at p. 480; Ranken et al, *J. Org. Chem.*, Vol. 54 [1989], at p. 2985, and Kentaro et al., *J. Heterocycl. Chem.*, Vol. 16 [1979] at p. 567). The sulfide can be oxidized to the sulfoxide or the sulfone. See, e.g., March, *Advanced Organic Chemistry*, (4th Ed., John Wiley and Sons, Inc., New York, N.Y., 1992). Alternatively, indoles (Ic) can be converted directly to sulfones of formula (Ih) (n=1) by treatment with phenylsulfonyl chloride (see, e.g., Dalton et al., *J. Chem. Soc., Perkin Trans. I* Vol. 10 [1983], at p. 2417.)

-continued

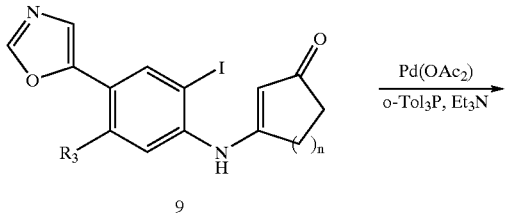

9

Scheme 4c

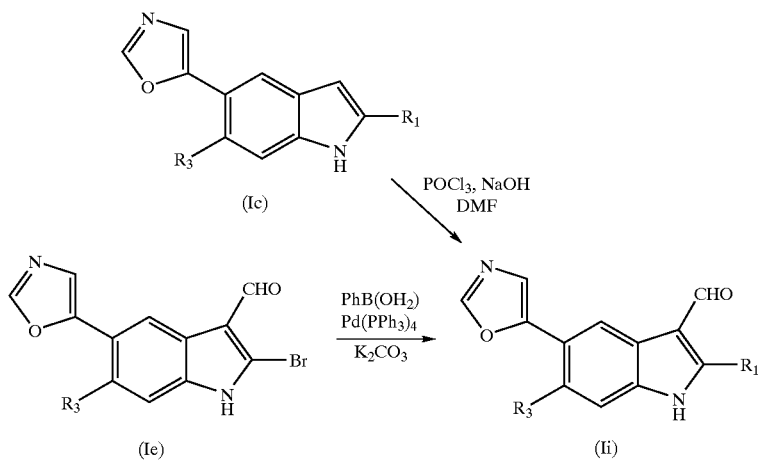

Scheme 4c represents a protocol for preparing compounds of formula (Ii), having an aldehyde functionality at the 3-position of the indole moeity. Treatment of indoles (Ic) with phosphorous oxychloride in a solvent such as DMF followed by treatment with a base like sodium hydroxide gives indoles (Ii). Alternatively, compounds of formula (Ii) can be prepared form brominated indoles (Ie) (see Scheme 3), using a Suzuki cross-coupling reaction.

Scheme 5

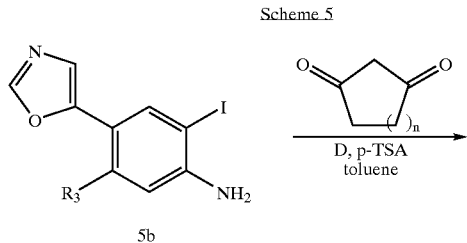

-continued

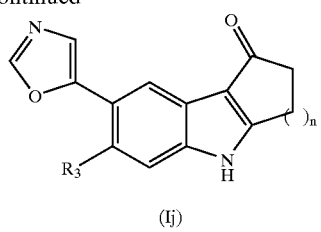

(Ij)

Cyclic-ketone indoles of formula (Ij) can be prepared as shown in Scheme 5 through Heck chemistry. Aniline (5b) is first treated with the appropriate 1,3-cyclicdione in an inert solvent such as toluene, xylene, or diphenylether in the presence of para-toluene sulfonic acid at a temperature up to its boiling point to give urethane (9). Subsequent Heck coupling conditions with palladium(II)acetate and tri-o-tolylphosphine in a solvent such as DMF at a temperature up to its boiling point provides indoles of formula (Ij). This method should be viable with non-cyclic 1,3-diones to form keto-indoles. Additionally, keto-indoles should be available from aldehydes (Ie) and (Ii) through an addition of a nucleophilic source such as an alkyl Grignard reagent or an alkyl lithium reagent. The resulting alcohol can then be oxidized to the keto-indole as described in Hudlicky, *Oxidations in Organic Chemistry*, cited above. An alternative approach to forming a methyl ketone at the 3-position involves the use of acetic anhydride or acetyl chloride in the presence of a Lewis acid such as $Et_2AlCl$, $TiCl_4$, or $AlCl_3$, or $ZnCl_2$. An example is described in Okauchi et al., *Organic Letters*, Vol. 2 (2000), at p. 1485.

The compounds of the present invention may be modified by appending appropriate functionalities to enhance selective biological properties. Such modifications are known in the art and include those which increase the compound's biological penetration into a given biological compartment (e.g. blood, lymphatic system, central nervous system), increase oral availability, increase solubility to allow administration by injection, alter metabolism, and alter rate of excretion. All such modifications are intended to encompassed within the spirit and scope of this invention.

Utility

The compounds of the present invention inhibit IMPDH enzyme and are thus useful in the treatment of disorders which are mediated by IMPDH. As used herein, the term "treating" or "treatment" refers to prophylaxis measures designed to inhibit or delay the onset of the disease or disorder and to responsive measures to alleviate, ameliorate, lessen, or cure the disease or disorder and/or its symptoms.

In view of their effects on inhibiting IMPDH activity, the compounds will be useful in treating consequences of many diseases associated with chronic and acute inflammation and immune-modulation. Such diseases include, but are not limited to, transplant rejection (e.g., kidney, liver, heart, lung, pancreas [e.g., islet cells], bone marrow, cornea, small bowel), skin allografts, skin homografts (such as employed in burn treatment), heart valve xenografts, serum sickness, graft vs. host disease, rheumatoid arthritis, psoriatic arthritis, traumatic arthritis, rubella arthritis, multiple sclerosis, juvenile diabetes, asthma, inflammatory bowel disease (such as Crohn's disease and ulcerative colitus), irritable bowel syndrome, pyoderma gangrenum, lupus (systemic lupus erythematosis), myasthenia gravis, psoriasis, dermatitis, dermatomyositis; eczema, seborrhoea, pulmonary inflammation, eye uveitis, hepatitis, Grave's disease, Hashimoto's thyroiditis, autoimmune thyroiditis, Behcet's or Sjorgen's syndrome (dry eyes/mouth), pernicious or immunohaemolytic anaemia, glomerulonephritis, scleroderma, morphea, lichen planus, viteligo (depigmentation of the skin), alopecia areata, autoimmune alopecia, autoimmune hypopituatarism, Guillain-Barre syndrome, alveolitis, osteoarthritis, osteoporosis, acute pancreatitis, chronic pancreatitis, Sezary's syndrome, migraine, cluster headaches, fever, sepsis, lupus (systematic lupus erythematosis), Alzheimer's Disease, Parkinson's disease, Creutzfeldt-Jacob disease, multiple sclerosis, and tuberculosis. The compounds may also be used to treat respiratory allergies and diseases including asthma, acute respiratory distress syndrome, hayfever, allergic rhinitis, and chronic obstructive pulmonary disease; and inflammatory disorders of the central nervous system, including HIV encephalitis, cerebral malaria, meningitis, and ataxia telangiectasis. Additionally, the compounds may be useful in treating pain, e.g., post-operative pain, neuromuscular pain, headache, pain caused by cancer, dental pain, and arthritis pain.

The inventive compounds also may be useful in the treatment of T-cell mediated hypersensitivity diseases, including contact hypersensitivity, delayed-type hypersensitivity, contact dermatitis (including that due to poison ivy), uticaria, skin allergies, respiratory allergies (hayfever, allergic rhinitis) and gluten-sensitive enteropathy (Celiac disease); in the treatment of fungal infections such as mycosis fungoides; and in the treatment of autoimmune or DNA or RNA viral replication diseases, such herpes simplex type 1 (HSV-1), herpes simplex type 2 (HSV-2), cytomegalovirus, Epstein-Barr, human immunodeficiency virus (HIV), Addison's disease (autoimmune disease of the adrenal glands), idiopathic adrenal insufficiency, autoimmune polyglandular disease (also known as autoimmune polyglandular syndrome), chronic active hepatitis or acute hepatitis infection (including hepatitis A, hepatits B, and hepatitis C), autoimmune gastritis, autoimmune hemolytic anemia, and autoimmune neutropenia.

Additionally, the inventive compounds will be useful in treating vascular diseases which have an inflammatory and or a proliferatory component. These diseases include but are not limited to atherosclerosis, transplant atherosclerosis, peripheral vascular disease, inflammatory vascular disease, intermittent claudication, restenosis, stenosis, cerebrovascular stroke, transient ischemic attack, myocardial ischemia and myocardial infarction.

The inventive compounds may be used in the treatment of cancer and tumor disorders, such as solid tumors, lymphomas and leukemia; and also more particularly, to treat cancer of the lung, prostate, colon, breast, ovaries, and bone, or angiogenic disorders including the formation or growth of solid tumors.

Additionally, IMPDH is also known to be present in bacteria and thus may regulate bacterial growth. As such, the IMPDH-inhibitor compounds of the present invention may be useful in treatment or prevention of bacterial infection, alone or in combination with other antibiotic agents.

The compounds of the invention may also be used to treat veterinary disease such as veterinary viral infections, including feline immunodeficiency virus, bovine immunodeficiency virus, and canine immunodeficiency virus.

The present invention also provides pharmaceutical compositions comprising at least one compound of formula I, or a salt thereof, capable of treating an IMPDH-associated disorder in an amount effective therefor, alone or in combination with at least one additional therapeutic agent, and any pharmaceutically acceptable carrier, adjuvant or vehicle. "Additional therapeutic agent" encompasses, but is not limited to, an agent or agents selected from the group consisting of an immunosuppressant, anti-cancer agent, anti-viral agent, anti-inflammatory agent, anti-fungal agent, antibiotic, anti-vascular hyperproliferation compound, potassium channel opener, calcium channel blocker, sodium hydrogen exchanger inhibitor, anti-arrhythmic agent, thrombin inhibitor, platelet aggregation inhibitor or anti-platelet agent, fibrinogen antagonist, diuretic, anti-hypertensive agent, mineralocorticoid receptor antagonist, phospodiesterase inhibitor, cholesterol/lipid lowering agent, anti-diabetic agent, angiogenesis modulator, anti-coagulant, anti-proliferative agent, anti-tumor agent, and/or anti-infective agent. In the methods of the present invention, such other therapeutic agent(s) may be administered prior to, simultaneously with or following the administration of the compound(s) of the present invention.

Examples of suitable other anti-inflammatory agents with which the inventive compounds may be used include aspirin, non-steroidal antiinflammatory drugs (NSAIDs) (such as ibuprofen and naproxin), TNF-α inhibitors (such as tenidap and rapamycin or derivatives thereof), or TNF-α antagonists (e.g., infliximab, OR1384), prednisone, dexamethasone, Enbrel®, cyclooxygenase inhibitors (i.e., COX-1 and/or COX-2 inhibitors such as Naproxen®, Celebrex®, or Vioxx®), CTLA4-Ig agonists/antagonists, CD40 ligand antagonists, other IMPDH inhibitors, such as mycophenolate (CellCept®), integrin antagonists, alpha-4 beta-7 integrin antagonists, cell adhesion inhibitors, interferon gamma antagonists, ICAM-1, prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, therapies for the treatment of irritable bowel syndrome (e.g., Zelmac® and Maxi-K® openers such as those disclosed in U.S. Pat. No. 6,184,231 B1), or NF-κB inhibitors, such as corticosteroids, calphostin, CSAIDs, 4-substituted imidazo [1,2-A]quinoxalines as disclosed in U.S. Pat. No. 4,200,750; Interleukin-10, glucocorticoids, salicylates, nitric oxide, and other immunosuppressants; and nuclear translocation inhibitors, such as deoxyspergualin (DSG).

Examples of suitable other antibiotics with which the inventive compounds may be used include cyclosporins (e.g., cyclosporin A), CTLA4-Ig, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and CD154 (a.k.a. "gp39"), such as antibodies specific for CD40 and/or CD 154, fusion proteins constructed from CD40 and/or CD154/gp39 (e.g., CD40Ig and CD8gp39), β-lactams (e.g., penicillins, cephalosporins and carbopenams); β-lactam and lactamase inhibitors (e.g., augamentin); aminoglycosides (e.g., tobramycin and streptomycin); macrolides (e.g., erythromycin and azithromycin); quinolones (e.g., cipro and tequin); peptides and deptopeptides (e.g. vancomycin, synercid and daptomycin) metabolite-based anti-biotics (e.g., sulfonamides and trimethoprim); polyring systems (e.g., tetracyclins and rifampins); protein synthesis inhibitors (e.g., zyvox, chlorophenicol, clindamycin, etc.); and nitro-class antibiotics (e.g., nitrofurans and nitroimidazoles).

Examples of suitable other antifungal agents with which the inventive compounds may be used include fungal cell wall inhibitors (e.g., candidas), azoles (e.g., fluoconazole and vericonazole), and membrane disruptors (e.g., amphotericin B).

Examples of suitable other antiviral agents for use with the inventive compounds include nucleoside-based inhibitors, protease-based inhibitors, viral-assembly inhibitors, and other antiviral agents such as abacavir.

Other additional therapeutic agents with which the inventive compounds may be used include antioxidants and/or lipid peroxidation inhibitors such as probucol, BO-653, Vitamin A, Vitamin E, and AGI-1067; antiosteoporosis agents such as alendronate and raloxifene; anviral agents for such as nucleoside-based inhibitors, protease-based inhibitors, and viral-assembly inhibitors; anti-osteoporosis agents such as alendronate, risedronate, PTH, PTH fragment, raloxifene, calcitonin, RANK ligand antagonists, calcium sensing receptor antagonists, TRAP inhibitors, selective estrogen receptor modulators (SERM) and AP-1 inhibitors; steriodal or non-steroidal progesterone receptor agonists ("PRA"), such as levonorgestrel, medroxyprogesterone acetate (MPA); anti-hypertensive agents such as beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, and spironolactone), renin inhibitors, ACE inhibitors (e.g., captopril, Vanlev®, pravachol, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), nitrates, and cardiac glycosides (e.g., digitalis and ouabain); phosphodiesterase (PDE) inhibitors that block the hydrolysis cAMP and/or cGMP including dipyridamole, cilostazol, sildenafil, rolipram, denbutyline, theophylline (1,2-dimethylxanthine), and ARIFLO™ (i.e., cis-4-cyano-4-[3-(cyclopentyloxy)-4-methoxyphenyl]cyclohexane-1-carboxylic acid), or PDE inhibitors in combination with anti-platelet agents; anticancer strategies and chemotherapies such as taxol and/or cisplatin; and antitumor agents such as paclitaxel, adriamycin, epithilones, cisplatin, and carboplatin.

The above other therapeutic agents, when employed in combination with the compounds of the present invention, may be used in the same dosage form with the compound of formula I, in different dosage forms, in those amounts indicated in the Physicians' Desk Reference (PDR), and/or as otherwise determined by one of ordinary skill in the art.

The compounds of the present invention may act in a synergistic fashion with one or more of the above agents to allow for increased efficacy and/or reduced doses of any of the above agents and therefore minimize potential hemorrhagic side-effects.

The term "pharmaceutically acceptable carrier, adjuvant or vehicle" refers to a carrier, adjuvant or vehicle that may be administered to a subject, together with a compound of the present invention, and which does not destroy the pharmacological activity thereof. Pharmaceutically acceptable carriers, adjuvants and vehicles that may be used in the pharmaceutical compositions of the present invention include, but are not limited to, the following: ion exchangers, alumina, aluminum stearate, lecithin, self-emulsifying drug delivery systems ("SEDDS") such as d(-tocopherol polyethyleneglycol 1000 succinate), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β- and γ-cyclodextrin, or chemically modified derivatives such as hydroxyalkylcyclodextrins, including 2- and 3-hydroxypropyl-β-cyclodextrins, or other solubilized derivatives may also be used to enhance delivery of the compounds of the present invention.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the formula I may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.1 to 500 mg/kg of body weight of active compound per day, which may be administered in a single dose or in the form of individual divided doses, such as from 1 to 5 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to IMPDH-associated disorders.

IMPDH Assay

The compounds disclosed herein are capable of targeting and inhibiting IMPDH enzyme. Inhibition can be measured by various methods, including, for example, IMP dehydrogenase HPLC assays (measuring enzymatic production of XMP and NADH from IMP and NAD) and IMP dehydrogenase spectrophotometric assays (measuring enzymatic production of NADH from NAD). See, e.g., Montero et al., Clinica Chimica Acta 238:169–178 (1995). Additional assays known in the art can be used in ascertaining the degree of activity of a compound ("test compound") as an IMPDH inhibitor. The inventors used the following assay to determine the degree of activity of the compounds disclosed herein as IMPDH inhibitors:

Activity of IMPDH I and IMPDH II was measured following an adaptation of the method described in WO 97/40028. The reaction mixture was prepared containing 0.1M Tris pH 8.0, 0.1 M KCl, 3 mM EDTA, 2 mM DTT, 0.4 mM IMP and 40 nM enzyme (IMPDH I or IMPDH II). The reaction was started by the addition of NAD to a final concentration of 0.4 mM. The enzymatic reaction was followed by measuring the increase in absorbance at 340 nM that results from the formation of NADH. For the analysis of potential inhibitors of the enzyme, compounds were dissolved in DMSO to a final concentration of 10 mM and added to the assay mixture such that the final concentration of DMSO was 2.5%. The assay was carried out in a 96-well plate format, with a final reaction volume of 200 $\mu$l.

Compounds disclosed herein are capable of inhibiting the enzyme IMPDH at a measurable level under the above-described assay and/or other assays known in the field.

The following examples illustrate preferred embodiments of the present invention and do not limit the scope of the present invention which is defined in the claims. Abbreviations employed in the Examples and Schemes previously set forth are defined below.

| Abbreviations | |
| --- | --- |
| aq. | Aqueous |
| Bn | Benzyl |
| Boc | tert-butoxycarbonyl |
| DCM | Dicholormethane |
| DMAP | Dimethylaminopyridine |
| DMF | dimethylformamide |
| DMSO | Dimethylsulfoxide |
| EDC | 1-(3-Dimethylaminopropyl)-3-ethylcarbodiimide hydrochloride |
| EtOAc | Ethyl acetate |
| Et | Ethyl |
| EtOH | Ethanol |
| h | Hours |
| HPLC | High pressure liquid chromatography |

| Abbreviations | |
|---|---|
| Lawesson's Reagent | [2,4-bis(4-methoxyphenyl)-1,3-dithia-2,4-diphosphetane-2-4-disufide |
| LC | liquid chromatography |
| Me | Methyl |
| MeOH | Methanol |
| min. | Minutes |
| MS | Mass spectrometry |
| n | normal |
| Pd/C | Palladium on carbon |
| Ph | Phenyl |
| Pr | Propyl |
| Ret t. | Retention time |
| RP | Reserve phase |
| rt or RT | room temperature |
| sat. | Saturated |
| Pd(PPh$_3$)$_4$ | tetrakis (triphenylphosphine) palladium |
| TEA | triethylamine |
| THF | Tetrahydrofuran |
| TFA | Trifluoroacetic acid |
| YMC | YMC Inc, Wilmington, NC 28403 |

In the Examples, conditions for determining analytical HPLC retention times are designated with parenthetical references following the times as follows:
(A): Column: YMC S5 ODS 4.6×50 mm; Solvent A=10% MeOH, 90% H$_2$O, 0.1% TFA; Solvent B=90% MeOH, 10% H$_2$O, 0.1% TFA);
(B): same as A using a YMC S5 ODSA 5 u 4.6×50 mm column;
(C): same as A using YMC S5 ODS-A 4.6×50 mm column;
(D): Column: YMC S5 ODS 4.6×50 mm Ballistic (4 min.); solvent A=10% MeOH, 90% H$_2$O, 0.2% H$_3$PO$_4$

EXAMPLE 1

2-Bromo-6-methoxy-5-(5-oxazolyl)-1H-indole-3-carboxaldehyde

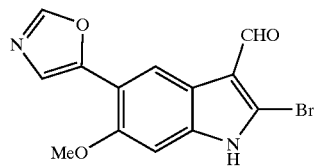

Step A: 1,3-Dihydro-6-methoxy-3-(methylthio)-5-(5-oxazolyl)-2H-indol-2-one

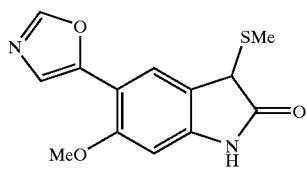

(1A)

To an oven-dried flask under a nitrogen atmosphere were sequentially added ethyl 2-(methylthio)acetate (3.4 mL, 26.31 mmol) and DCM (150 mL). The contents of the flask were cooled to −78° C., and sulfuryl chloride (1.0M in DCM, 26.31 mL, 26.31 mmol) was added over a three-minute period. The reaction mixture was stirred at −78° C. for fifteen minutes. A mixture of proton-sponge (5.64 g, 26.31 mmol) and 5-(4-Amino-2-methoxyphenyl)oxazole (WO 9740028) (5 g, 26.31 mmol) in DCM (100 mL) was added dropwise over a period of one hour. The reaction mixture was stirred at −78° C. for two hours and quenched by the addition of TEA (3.7 mL, 26.31 mmol). The reaction mixture was allowed to warm to rt, stirred for one hour, and partitioned between DCM and water (100 mL). The DCM layer was dried over sodium sulfate and concentrated under reduced pressure. To the residue was added acetic acid (150 mL), and the contents were stirred at rt for eighteen hours. The reaction mixture was concentrated and purified by silica gel column chromatography to provide compound 1A (4.7 g, 65%). HPLC Ret. t=2.45 min. (A); LC/MS M$^{+1}$=277.10.

Step B: 2-Bromo-6-methoxy-5-(5-oxazolyl)-1H-indole-3-carboxaldehyde

To compound 1A (1.7 g) in EtOH (20 mL) was added Raney-Ni, and the contents were refluxed for sixty hours. The reaction mixture was filtered over Celite while hot, and the Celite pad was washed with additional EtOH (2×10 mL). The filtrate was concentrated under reduced pressure to yield a solid (0.7 g), which was used as such for the subsequent step without further purification.

To a solution of phosphorous oxybromide (2.18 g, 7.6 mmol) in chloroform (20 mL) was added DMF (0.7 mL, 9.12 mmol) at 0° C. over a five minute period. This was followed by the addition of the solid compound obtained above at room temperature. The reaction mixture was stirred at rt overnight and quenched by the slow addition of 1N sodium hydroxide (20 mL). The reaction mixture was transferred into a separating funnel, and the chloroform layer was collected, dried over sodium sulfate, concentrated, and purified by silica gel flash chromatography to provide the title compound (0.06 g, 5%). HPLC Ret. t=2.84 min. (A); LC/MS M$^{+1}$=320.92

EXAMPLE 2

6-Methoxy-5-(5-oxazolyl)-2-phenyl-1H-indole-3-carboxaldehyde

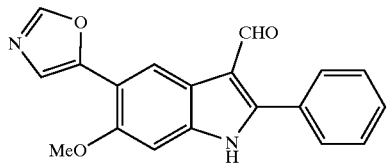

To a solution of Example 1 (0.02 g, 0.06 mmol) in anhydrous dimethoxyethane were sequentially added potassium carbonate (0.016 g, 0.11 mmol), phenylboronic acid (0.017 g, 0.135 mmol), and Pd(PPh$_3$)$_4$ (0.007 g, 0.006 mmol). The contents of the flask were purged with nitrogen for five minutes and heated at 80° C. for eighteen hours. The yellow reaction mixture was cooled to rt and purified by silica gel column chromatography to provide Example 2 (0.013 g, 66%). HPLC Ret. t=3.15 min. (B); LC/MS M$^{+1}$= 319.09

EXAMPLE 3

2-Benzo[b]thien-3-yl-6-methoxy-5-(5-oxazolyl)-1H-indole-3-carboxaldehyde

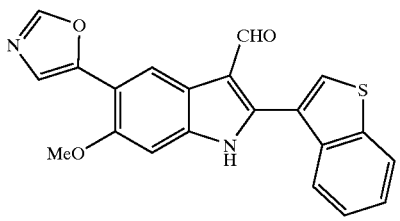

Example 3 was prepared in a manner analogous to Example 2 starting with 2-Bromo-6-methoxy-5-(5-oxazolyl (Example 1) (0.02 g, 0.06 mmol) and benzothiophene-3-boronic acid. Yield: 0.023 g (99%). HPLC Ret. t=3.45 min. (A); LC/MS M$^{+1}$=375.01.

EXAMPLE 4

6-Methoxy-5-(5-oxazolyl)-2-(phenylmethyl)-1H-indole

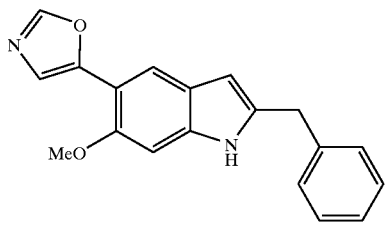

Step A: 5-Methoxy-4-(5-oxazolyl)-2-(3-phenyl-1-propynyl)benzenamine

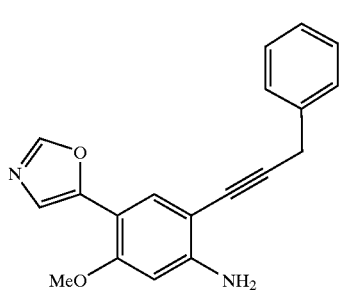

(4A)

To a solution of 5-(4-amino-5-iodo-2-methoxyphenyl)oxazole (WO 0181340) (0.4 g, 1.26 mmol) in anhydrous DMF (2 mL) were sequentially added 3-phenyl-1-propyne (0.19 mL, 1.5 mmol), TEA (6 mL), copper(I)iodide (0.019 g, 0.1 mmol), and bis(triphenylphosphine) palladiumdichloride (0.035 g, 0.05 mmol). The reaction mixture was purged with nitrogen for ten minutes, heated at 80° C. for two hours, concentrated under reduced pressure, and purified by silica gel column chromatography to provide compound 4A (0.34 g, 88%). HPLC Ret. t=3.69 min. (C); LC/MS M$^{+1}$=305.10.
Step B: 6-Methoxy-5-(5-oxazolyl)-2-(phenylmethyl)-1H-indole
To compound (4A) (0.3 g, 0.98 mmol) in N-methylpyrrolidine (3 mL) was added potassium tert-butoxide (0.15 g, 1.32 mmol), and the contents were heated at 80° C. for two hours. The reaction mixture was cooled to rt and partitioned between EtOAc (2×40 mL) and brine (40 mL). The EtOAc layer was dried over sodium sulfate, concentrated, and purified by silica gel chromatography to yield the title compound (0.18 g, 60%). HPLC Ret. t=3.56 min. (A); LC/MS M$^{+1}$=305.32.

EXAMPLE 5

6-Methoxy-5-(5-oxazolyl)-2-(phenylmethyl)-1H-indole-3-carboxaldehyde

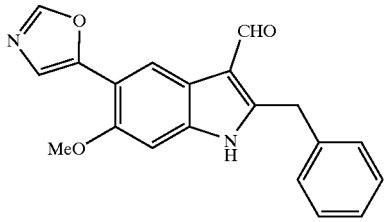

To anhydrous DMF (3 mL) at rt was added phosphorous oxychloride (25 µl, 0.26 mmol). The contents were stirred for fifteen minutes, and Example 4 was added as a solid. The reaction mixture was stirred at rt for an additional forty-five minutes. Sodium hydroxide (5 mL, 1N) was added, and the contents were heated at 80° C. for ten minutes. The reaction mixture was cooled to rt, and the solid precipitate was filtered, washed with water (3×10 mL), washed with a minimum amount of EtOH, and dried to provide the title compound (0.038 g, 70%). HPLC Ret. t=3.09 min. (B); LC/MS M$^{+1}$=333.13.

EXAMPLE 6

6-Methoxy-5-(5-oxazolyl)-2-(phenylmethyl)-1H-indole-3-carbonitrile

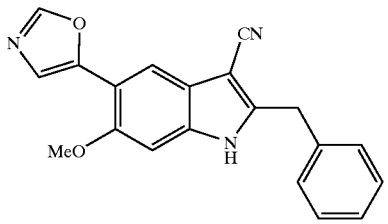

To a solution of Example 4 (0.05 g, 0.16 mmol) in acetonitrile (2 mL) was added chlorosulfonyl isocyanate (14 µL, 0.16 mmol) at 0° C. The reaction mixture was stirred at 0° C. for thirty minutes. Anhydrous DMF (14 µl, 0.176 mmol) was added, the contents were stirred at rt for forty-five minutes, then 1N NaOH (1 mL) was added, with subsequent heating at 80° C. for five minutes. The reaction mixture was cooled to rt, and the solid precipitate was filtered, washed with water (10 mL), washed with a minimum amount of EtOH, and dried to provide the title compound (0.036 g, 67%). HPLC Ret. t=3.35 min. (B); LC/MS M$^{+1}$=330.16.

EXAMPLE 7

6-Methoxy-5-(5-oxazolyl)-2-phenyl-1H-indole

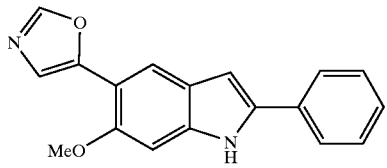

Step A: 5-Methoxy-4-(5-oxazolyl)-2-(phenylethynyl)benzenamine

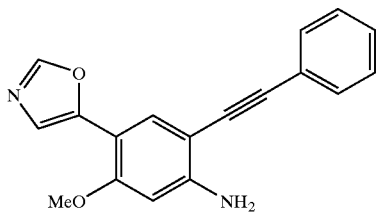
(7A)

Compound 7A was prepared in a manner analogous to compound 4A starting with 0.04 g of 5-(4-amino-5-iodo-2-methoxyphenyl)oxazole (WO 0181340) and substituting 3-phenyl-1-propyne with phenyl acetylene. Yield: 0.365 g (99%). HPLC Ret. t=3.48 min. (A); LC/MS $M^{+1}$=291.06

Step B: 6-Methoxy-5-(5-oxazolyl)-2-phenyl-1H-indole

The procedure of Step 4B was followed starting with 0.35 g of compound 7A and 0.243 g of potassium tert-butoxide to give Example 7. Yield: 0.215 g (61%). HPLC Ret. t=3.85 min. (C); LC/MS $M^{+1}$=291.12.

EXAMPLE 8

6-Methoxy-5-(5-oxazolyl)-2-phenyl-1H-indole-3-carbonitrile

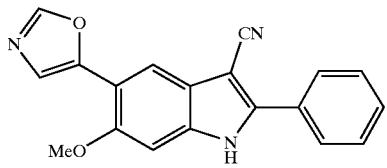

The same or similar procedure as described for Example 6 was followed, starting with 0.05 g of Example 7 and and 30 µL of chlorosulfonyl isocyanate to give Example 8. Yield: 0.035 g (64%). HPLC Ret. t=3.62 min. (C); LC/MS $M^{+1}$= 315.98.

EXAMPLE 9

2-Benzo[b]thien-3-yl-6-methoxy-5-(5-oxazolyl)-1H-indole

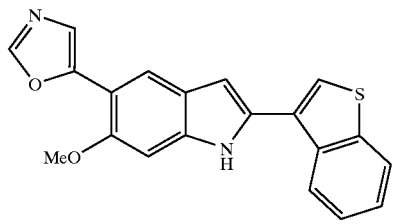

Step A: Benzo[b]thien-3-ylethynyl)trimethylsilane

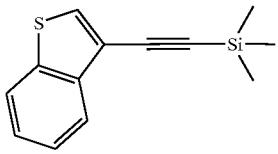
(9A)

Compound 9A was prepared in a manner analogous to compound 4A starting with 1.0 g of 3-bromo benzothiophene and substituting 3-phenyl-1-propyne with trimethylsilyl acetylene. Yield: 1.1 g (99%).

Step B: 3-Ethynylbenzo[b]thiophene

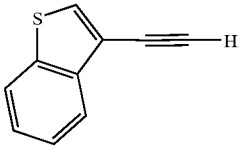
(9B)

To a solution of compound 9A (1.1 g, 5.65 mmol) in anhydrous THF (10 mL) was added tetrabutylammonium fluoride (6.8 mL of a 1.0 M solution in THF, 6.78 mmol) at rt. The reaction mixture was stirred at rt for forty-five minutes, concentrated under reduced pressure, and partitioned between EtOAc (50 mL) and brine (30 mL). The EtOAc layer was dried over sodium sulfate, concentrated, and purified by silica gel chromatography to provide 9B (0.85 g, 95%).

Step C: 2-(Benzo[b]thien-3-ylethynyl)-5-methoxy-4-(5-oxazolyl)benzenamine

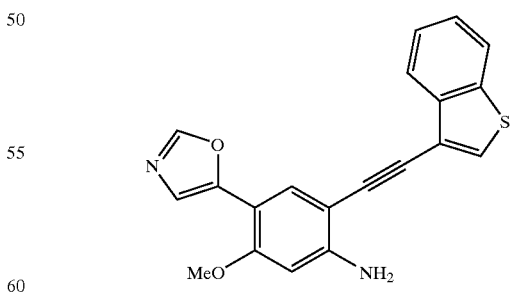

The procedure described above for preparing compound 4A was followed, using 1.4 g of 5-(4-amino-5-iodo-2-methoxyphenyl)oxazole (WO 0181340) and substituting 3-phenyl-1-propyne with 3-ethynylbenzo[b]thiophene. Yield: 1.4 g (88%). HPLC Ret. t=4.02 min. (C); LC/MS $M^{+1}$=347.07.

Step D: 2-Benzo[b]thien-3-yl-6-methoxy-5-(5-oxazolyl)-1H-indole

Example 9 was prepared following the process of Step 4B, starting with 0.95 g of compound 9C and 0.554 g of potassium tert-butoxide. Yield: 0.215 g (60%). HPLC Ret. t=3.96 min. (A); LC/MS M$^{+1}$=347.36.

EXAMPLE 10

2-Benzo[b]thien-3-Y1-6-methoxy-5-(5-oxazolyl)-1H-indole-3-carbonitrile

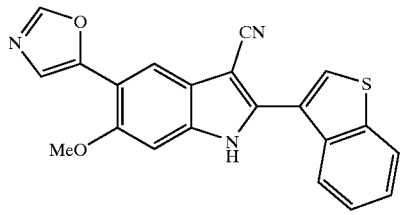

Example 10 was prepared in a manner analogous to example 6 starting with 0.025 g of Example 9 and 6 μL of chlorosulfonyl isocyanate. Yield: 0.006 g (23%). HPLC Ret. t=3.58 min. (A); LC/MS M$^{+1}$=372.34.

EXAMPLE 11

6-Methoxy-5-(5-oxazolyl)-2-(4-thiazolyl)-1H-indole

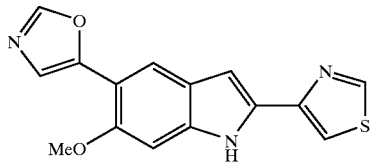

Step A: 4-[(Trimethylsilyl)ethynyl]thiazole

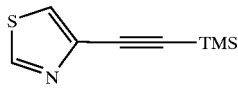
(11A)

Compound 11A was prepared following step 4A starting with 0.59 g of 4-bromothiazole and substituting 3-phenyl-1-propyne with trimethylsilyl acetylene. Yield: 0.475 g (72%).

Step B: (4-Ethynylthiazole)

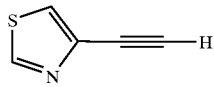
(11B)

Compound 11B was prepared following Step 9B starting with 0.475 g of compound 11A. Yield: 0.118 g (41%).

Step C: 6-Methoxy-5-(5-oxazolyl)-2-(4-thiazolyl)-1H-indole

To a solution of 5-(4-amino-5-iodo-2-methoxyphenyl)oxazole (WO 0181340) (0.293 g, 0.93 mmol) in diethylamine (2.5 mL) was added 4-ethynylthiazole (0.118 g, 1.08 mmol) and bis(triphenylphosphine)palladiumdichloride (0.019 g, 0.027 mmol). The contents were purged with nitrogen and heated in a steel bomb at 120° C. for 20 minutes. The reaction mixture was cooled to rt and purified by silica gel column chromatography to provide the title compound (0.065 g, 20%). HPLC Ret. t=2.79 min. (A); LC/MS M$^{+1}$=298.27.

EXAMPLE 12

1,2,3,9-Tetrahydro-7-methoxy-6-(5-oxazolyl) 4H-carbazol-4-one

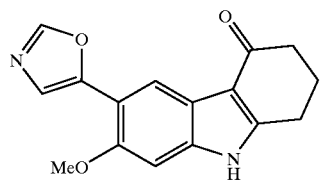

Step A: 3-[[2-Iodo-5-methoxy-4-(5-oxazolyl)phenyl]amino]-2-cyclohexen-1-one

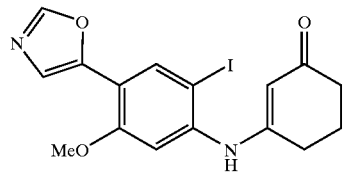

A mixture of 5-(4-amino-5-iodo-2-methoxyphenyl)oxazole (WO 0181340) (0.250 g, 0.791 mmol), 1,3-cyclohexanedione (0.089 g, 0.791 mmol), and p-toluenesulfonic acid (0.030 g, 0.158 mmol) in 20 mL of dry toluene was heated at reflux in a Dean-Stark apparatus overnight. The toluene was removed under reduced pressure, and the resulting residue was dissolved in DCM, washed with water, and dried over anhydrous sodium sulfate. Concentration under reduced pressure followed by purification by silica gel chromatography afforded 12A (0.205 g, 63%) as a yellow solid. HPLC Ret. t.=of 2.74 min. (D); LC/MS M$^{+1}$=411.17.

Step B: 1,2,3,9-Tetrahydro-7-methoxy-6-(5-oxazolyl) 4H-carbazol-4-one

To a flask containing palladium (II) acetate (0.020 g, 0.090 mmol) and tri-o-tolylphosphine (0.057 g, 0.186 mmol) under nitrogen was added anhydrous DMF (0.89 mL). The mixture was stirred for 1 h at rt, and 329 μL of this catalyst solution was added to a sealed tube of compound 12A (0.070 g, 0.171 mmol) in 0.6 mL of anhydrous DMF. The mixture was degassed (3x), then TEA was added, and the reaction mixture was heated at 120° C. for 15 hr. The reaction was cooled, filtered through cotton, and concentrated under reduced pressure. Purification by silica gel chromatography afforded the title compound (0.042 g, 86%) as a tan solid. HPLC Ret. t.=2.42 min. (D); a LC/MS M$^{+1}$=283.23.

EXAMPLE 13

3,4-Dihydro-6-methoxy-7-(5-oxazolyl) cyclopent[b]indol-1(2H)-one

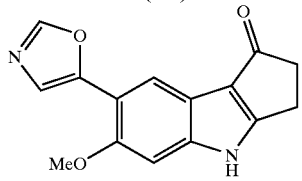

Step A: 3-[[2-Iodo-5-methoxy-4-(5-oxazolyl)phenyl]amino]2-cyclopenten-1-one

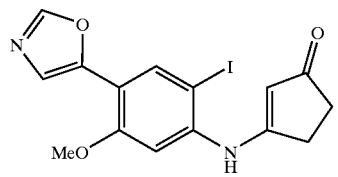
(13A)

A mixture of 5-(4-amino-5-iodo-2-methoxyphenyl) oxazole (WO 0181340) (0.250 g, 0.791 mmol), 1,3-cyclopentanedione (0.078 g, 0.791 mmol), and p-toluenesulfonic acid (0.030 g, 0.158 mmol) in 20 mL of dry toluene was heated at reflux in a Dean-Stark apparatus overnight. The toluene was removed under reduced pressure, and the resulting residue was dissolved in DCM, washed with water, and dried over anhydrous sodium sulfate. Concentration under reduced pressure followed by purification by silica gel chromatography afforded compound 13A (0.201 g, 64%) as a yellow solid. HPLC Ret. time=2.48 min. (D); LC/MS $M^{+1}$=397.11.

Step B: 3,4-Dihydro-6-methoxy-7-(5-oxazolyl) cyclopent[b]indol-1(2H)-one

The same or similar process described for Step 12B was followed, using 611 µL of the catalyst solution and 126 g (0.218 mmol) of compound 13A in 0.8 mL of anhydrous DMF. Purification by silica gel chromatography afforded the title compound (0.077 g, 91%) as a tan solid. HPLC Ret. t.=2.30 min. (D); LC/MS $M^{+1}$=269.11.

Although the present invention has been described in some detail by way of illustration and example for purposes of clarity and understanding, it will be apparent that certain changes and modifications may be practiced within the scope of the appended claims. All examples are illustrative of the present invention and are not to be construed as limiting of the scope or embodiments of the appended claims.

We claim:
1. A compound having the formula (I),

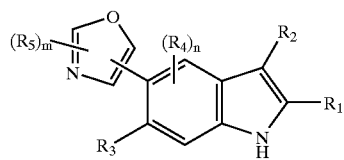
(I)

or a pharmaceutically-acceptable salt, hydrate, or prodrug thereof, wherein:
$R_1$ is selected from optionally-substituted aryl, heteroaryl, arylkyl, and heteroarylalkyl;
$R_2$ is selected from hydrogen, halogen, cyano, alkyl, substituted alkyl, —C(═O)$R_6$, —CO$_2R_6$, —S(═O)$R_7$, —SO$_2R_7$, —SO$_3R_7$, —OR$_6$, —SR$_6$, —NR$_6R_7$, —C(═O)NR$_6R_7$, —NR$_6$C(═O)$R_7$, NR$_6$CO$_2R_7$, —NR$_6$SO$_2R_7$, —SO$_2$NR$_6R_7$, cycloalkyl, aryl, heterocyclo and heteroaryl,
or alternatively, $R_1$ and $R_2$ taken together from an optionally-substituted fused (C$_{5-6}$)carbocyclic ring or five-to-six membered heterocyclo ring;
$R_3$ is alkyl, substituted alkyl, alkoxy, haloalkoxy, or halogen;
$R_4$ and $R_5$ are independently selected from alkyl, substituted alkyl, halogen, cyano, and —OR$_9$;
$R_6$ and $R_7$ are selected from hydrogen, alkyl, substituted alkyl, cycloalkyl, aryl, heterocyclo, and heteroaryl, except $R_7$ is not hydrogen when attached to a sulfonyl group as in —S(═O)$R_7$, —SO$_2R_7$, and —SO$_3R_7$;
$R_9$ is hydrogen, $C_{1-6}$alkyl, substituted $C_{1-6}$alkyl, cycloalkyl, aryl, heterocyclo, or heteroaryl; and
m and n are 0, 1 or 2.

2. A compound according to claim 1, or a pharmaceutically-acceptable salt, hydrate, or prodrug thereof, wherein:
$R_2$ is selected from halogen, cyano, alkyl, substituted alkyl, —C(═O)$R_6$, —CO$_2R_6$, —SR$_6$, —S(═O)$R_7$, —SO$_2R_7$, —SO$_3R_7$, cycloalkyl, aryl, heterocyclo and heteroaryl, provided, however that $R_2$ does not comprise an alkyl substituted with NR$_{18}R_{19}$, wherein $R_{18}$ and $R_{19}$ are selected from hydrogen, alkyl, arylalkyl, heteroarylalkyl, carboxyalkyl, and C(═O)arylalkyl.

3. A compound according to claim 2, or a pharmaceutically-acceptable salt, hydrate, or prodrug thereof, wherein $R_3$ is O(C$_{1-4}$alkyl) or OCF$_3$.

4. A compound according to claim 1, or a pharmaceutically-acceptable salt, hydrate, or prodrug thereof, wherein
$R_1$ is

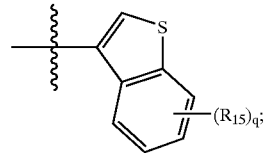

$R_{15}$ is selected from alkyl, alkenyl, halogen, haloalkyl, haloalkoxy, cyano, nitro, amino, alkylamino, aminoalkyl, hydroxy, hydroxyalkyl, alkoxy, and alkylthio;
and q is 0, 1 or 2.

5. A compound according to claim 4, or a pharmaceutically-acceptable salt, hydrate, or prodrug thereof, wherein $R_2$ is cyano.

6. A compound having the formula (I),

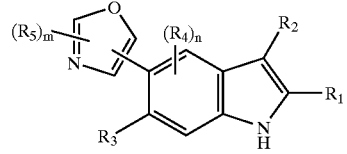
(I)

or a pharmaceutically-acceptable salt, hydrate, or prodrug thereof, wherein:
$R_1$ is independently selected from halogen, aryl, heteroaryl, arylalkyl, or heteroarylalkyl, and
$R_2$ is independently selected from hydrogen, halogen, cyano, —C(═O)$R_6$, —CO$_2R_6$, —SR$_6$, —S(═O)$R_7$, —SO$_2R_7$, and —SO$_3R_7$,
or alternatively, $R_1$ and $R_2$ taken together form a fused (C$_{5-6}$)carbocyclic ring or a fused five-to-six membered heterocyclo ring, said ring being optionally substituted with one to two groups selected from $R_8$;

R$_3$ is C$_{1-6}$alkyl, halo(C$_{1-4}$alkyl), O(C$_{1-6}$alkyl), halo(C$_{1-4}$alkoxy), or halogen;

R4 and R$_5$ are independently selected from C$_{1-6}$alkyl, substituted C$_{1-6}$alkyl, halogen, cyano, and —OR$_9$;

R$_6$ and R$_7$ are selected from hydrogen, C$_{1-6}$alkyl, substituted C$_{1-6}$alkyl, cycloalkyl, aryl, heterocyclo, and heteroaryl, except R$_7$ is not hydrogen;

R$_8$ is selected from C$_{1-6}$alkyl, substituted C$_{1-6}$alkyl, halogen, keto (=O), cyano, —OR$_{11}$, —SR$_{11}$, —NR$_{11}$R$_{12}$, —(C=O)R$_{11}$, —CO$_2$R$_{11}$, —C(=O)NR$_{11}$R$_{12}$, —NR$_{11}$C(=O)R$_{12}$, NR$_{11}$CO$_2$R$_{12}$, —OC(=O)R$_{11}$, —OC(=O)NR$_{11}$R$_{12}$, —NR$_{11}$C(=O)NR$_{12}$R$_{13}$, NR$_{11}$SO$_2$R$_{14}$, —SO$_2$NR$_{11}$R$_{12}$, SO$_2$R$_{14}$, SO$_3$R$_{14}$, cycloalkyl, aryl, heteroc heteroaryl;

R$_9$ is selected from hydrogen, C$_{1-6}$alkyl, substituted C$_{1-6}$alkyl, cycloalkyl, aryl, heterocyclo, and heteroaryl;

R$_{11}$, R$_{12}$, R$_{13}$ and R$_{14}$ are selected from hydrogen, C$_{1-6}$alkyl, cycloalkyl, aryl, heterocyclo, heteroaryl, and C$_{1-6}$alkyl substituted with one, two or three of halogen, hydroxy, O(alkyl), O(phenyl), O(benzyl), nitro, cyano, —(C=O)H, —CO$_2$H, —(C=O)alkyl, —CO$_2$alkyl, —NH$_2$, —NH(alkyl), —NH(cycloalkyl), —NH(aryl), —NH(heterocyclo), —N(alkyl)$_2$, —C(=O)phenyl, —(C=O)NH$_2$, —(C=O)NH(alkyl), —(C=O)NH(cycloalkyl), —(C=O)N(alkyl)$_2$, phenyl, benzyl, C$_{3-7}$cycloalkyl, four to seven membered heterocyclo, and/or five or six membered heteroaryl, provided, however, that R$_{14}$ is not hydrogen when attached to a sulfonyl group as in —SO$_2$R$_{14}$ and —SO$_3$R$_{14}$; and m and n are 0, 1 or 2.

7. A compound according to claim 6, or a pharmaceutically-acceptable salt, hydrate, or prodrug thereof, wherein R$_1$ is selected from phenyl, thienyl, thiazolyl, benzothienyl, and benzyl, and is optionally substituted with one to two R$_{15}$; and R$_{15}$ is selected from alkyl, alkenyl, halogen, haloalkyl, haloalkoxy, cyano, nitro, phenyl, benzyl, amino, alkylamino, aminoalkyl, hydroxy, hydroxyalkyl, alkoxy, alkylthio, phenyloxy, and benzyloxy.

8. A compound according to claim 6, or a pharmaceutically-acceptable salt, hydrate, or prodrug thereof, wherein R$_3$ is O(C$_{1-4}$alkyl) or OCF$_3$.

9. A compound according to claim 6, or a pharmaceutically-acceptable salt, hydrate, or prodrug thereof, having the formula (Ia),

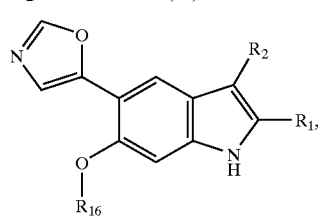
(Ia)

wherein

R$_1$ is selected from phenyl, thienyl, thiazolyl, benzothienyl, and benzyl, and is optionally substituted with one to two R$_{15}$;

R$_{15}$ is selected from alkyl, alkenyl, halogen, haloalkyl, haloalkoxy, cyano, nitro, phenyl, benzyl, amino, alkylamino, aminoalkyl, hydroxy, hydroxyalkyl, alkoxy, alkylthio, phenyloxy, and benzyloxy; and R$_{16}$ is selected from methyl, ethyl, and CF$_3$.

10. A compound according to claim 9, or a pharmaceutically-acceptable salt, hydrate, or prodrug thereof, wherein R$_1$ is

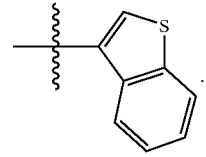

11. A compound having the formula (Ia),

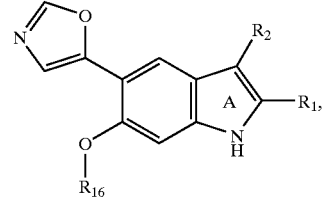
(Ia)

or a pharmaceutically-acceptable salt, hydrate, or prodrug thereof, wherein

R$_1$ is independently selected from halogen, phenyl, thienyl, thiazolyl, benzothienyl, and benzyl, and is optionally substituted with one to two R$_{15}$;

R$_2$ is independently selected from hydrogen, halogen, cyano, —C(=O)R$_6$, and —CO$_2$R$_6$, or alternatively, R$_1$ and R$_2$ taken together form

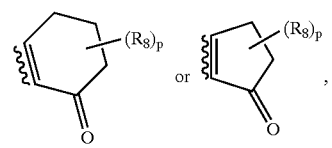

which is fused to ring A sharing a common double bond therewith along the bond region designated with the symbol R$_6$ is selected from hydrogen and C$_1$–C$_4$alkyl;

R$_8$ and R$_{15}$ are at each occurrence independently selected from alkyl, alkenyl, halogen, haloalkyl, haloalkoxy, cyano, nitro, phenyl, benzyl, amino, alkylamino, aminoalkyl, hydroxy, hydroxyalkyl, alkoxy, alkylthio, phenyloxy, and benzyloxy;

R$_{16}$ is selected from C$_1$–C$_4$alkyl and haloC$_1$–C$_4$alkyl; and p is 0, 1 or 2.

12. A compound according to claim 11, or a pharmaceutically-acceptable salt, hydrate, or prodrug thereof, wherein R$_1$ is

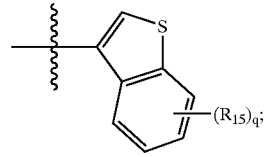

R$_{16}$ is methyl or ethyl; and q is 0, 1 or 2.

13. A pharmaceutical composition comprising an effective amount of at least one compound according to claim 1, or a salt, hydrate or prodrug thereof, and a pharmaceutically acceptable carrier, adjuvant or vehicle.

* * * * *

UNITED STATES PATENT AND TRADEMARK OFFICE
CERTIFICATE OF CORRECTION

| | |
|---|---|
| PATENT NO. | : 7,008,958 B2 |
| APPLICATION NO. | : 10/441849 |
| DATED | : March 7, 2006 |
| INVENTOR(S) | : Scott Hunter Watterson, T.G. Murali Dhar and Edwin J. Iwanowicz |

It is certified that error appears in the above-identified patent and that said Letters Patent is hereby corrected as shown below:

On the Title page at section (75) Inventors: "Iwan wicz" should be replaced with -- Iwanowicz --.

Signed and Sealed this

Fifth Day of December, 2006

JON W. DUDAS
*Director of the United States Patent and Trademark Office*